US012605058B2

(12) United States Patent
Mock et al.

(10) Patent No.: US 12,605,058 B2
(45) Date of Patent: Apr. 21, 2026

(54) REMOTE MEDICAL EXAMINATION

(71) Applicants:Presley M. Mock, Dallas, TX (US);
Lynn Parr Mock, Dallas, TX (US)

(72) Inventors: Presley M. Mock, Dallas, TX (US);
Lynn Parr Mock, Dallas, TX (US)

( * ) Notice: Subject to any disclaimer, the term of this
patent is extended or adjusted under 35
U.S.C. 154(b) by 0 days.

(21) Appl. No.: 18/773,662

(22) Filed: Jul. 16, 2024

(65) Prior Publication Data

US 2024/0366079 A1     Nov. 7, 2024

Related U.S. Application Data

(63) Continuation of application No. 17/453,169, filed on
Nov. 1, 2021, now Pat. No. 12,070,194.
(Continued)

(51) Int. Cl.
| | |
|---|---|
| *A61B 1/24* | (2006.01) |
| *A61B 1/06* | (2006.01) |
| *A61B 1/227* | (2006.01) |
| *A61B 1/233* | (2006.01) |
| *A61B 1/32* | (2006.01) |

(Continued)

(52) U.S. Cl.
CPC .................. *A61B 1/24* (2013.01); *A61B 1/06*
(2013.01); *A61B 1/227* (2013.01); *A61B 1/233*
(2013.01); *A61B 1/32* (2013.01); *G16H 40/67*
(2018.01); *H04N 7/183* (2013.01); *H04N*
*23/56* (2023.01)

(58) Field of Classification Search
None
See application file for complete search history.

(56) References Cited

U.S. PATENT DOCUMENTS

| | | |
|---|---|---|
| 6,295,506 B1 | 9/2001 | Heinonen et al. |
| 8,200,277 B2 | 6/2012 | Lee |
| | (Continued) | |

FOREIGN PATENT DOCUMENTS

| | | |
|---|---|---|
| WO | WO 2015/195879 A1 | 12/2015 |
| WO | WO 2016/013760 A1 | 1/2016 |
| WO | WO 2018/159893 A1 | 9/2018 |

OTHER PUBLICATIONS

International Search Report and Written Opinion issued by the
United States Patent and Trademark Office as International Search-
ing Authority for International Application No. PCT/US2021/
072187 dated Mar. 1, 2022. (9 pages).

*Primary Examiner* — Shadan E Haghani
(74) *Attorney, Agent, or Firm* — Haynes and Boone, LLP

(57)     ABSTRACT

The present disclosure relates to remote medical examina-
tion of a patient, and, more specifically, to a remote exam
attachment that, along with a user device, may capture
images of an anatomical feature for examination of a patient.
The remote exam attachment may include a lens and may
couple to an examination tool, such as a speculum, a scope,
or a tongue depressor, which may be used with a camera of
the user device. The user device may be configured to adjust
one or more settings of the camera, such as the zoom, field
of view, aperture, and/or the like. The user device may
further be configured to transmit an image captured in
conjunction with the remote exam attachment to another
user device. Accordingly, the remote exam attachment,
along with the user device, may capture, display, and/or
transmit images of an anatomical feature, facilitating remote
examination of a patient.

19 Claims, 22 Drawing Sheets

Related U.S. Application Data

(60) Provisional application No. 63/198,668, filed on Nov. 2, 2020.

(51) Int. Cl.
| | |
|---|---|
| *G16H 40/67* | (2018.01) |
| *H04N 7/18* | (2006.01) |
| *H04N 23/56* | (2023.01) |

(56) References Cited

U.S. PATENT DOCUMENTS

| | | | |
|---|---|---|---|
| 8,786,695 B2 | 7/2014 | Fletcher et al. | |
| 8,998,609 B2 | 4/2015 | Prakash et al. | |
| 9,042,586 B2 | 5/2015 | Burns et al. | |
| 9,094,493 B2 | 7/2015 | Quilter et al. | |
| 9,195,023 B2 | 11/2015 | O'Neill et al. | |
| D746,802 S | 1/2016 | Mulumudi et al. | |
| 9,241,663 B2 | 1/2016 | Jena et al. | |
| 9,282,288 B2 | 3/2016 | Hillier et al. | |
| 9,325,884 B2 | 4/2016 | Fletcher et al. | |
| 9,350,956 B2 | 5/2016 | Quilter et al. | |
| 9,414,155 B2 | 8/2016 | Mulumudi et al. | |
| 9,445,713 B2 | 9/2016 | Douglas et al. | |
| 9,451,874 B2 | 9/2016 | Bromwich | |
| 9,474,489 B2 | 10/2016 | Poplaw | |
| D772,215 S | 11/2016 | Mulumudi et al. | |
| 9,538,927 B2 | 1/2017 | Thaveeprungsriporn et al. | |
| 9,560,968 B2 | 2/2017 | Lim et al. | |
| 9,602,917 B2 | 3/2017 | Mulumudi et al. | |
| 9,661,200 B2 | 5/2017 | O'Neill et al. | |
| 9,706,918 B2 | 7/2017 | Myung et al. | |
| 9,706,975 B2 | 7/2017 | Mulumudi et al. | |
| 9,833,140 B2 | 12/2017 | Zhou | |
| 9,839,352 B2 | 12/2017 | Wallace et al. | |
| 9,855,019 B2 | 1/2018 | Mulumudi et al. | |
| 9,939,714 B1 | 4/2018 | Matthews | |
| 10,092,182 B2 | 10/2018 | Myung et al. | |
| 10,092,243 B2 | 10/2018 | Mirza et al. | |
| 10,117,574 B2 | 11/2018 | Zhou | |
| 10,129,450 B2 | 11/2018 | Nabhan | |
| 10,182,757 B2 | 1/2019 | Gareau et al. | |
| 10,265,023 B2 | 4/2019 | Roh et al. | |
| 10,271,816 B2 | 4/2019 | Mulumudi et al. | |
| 10,285,578 B2 | 5/2019 | Desgranges et al. | |
| 10,292,583 B2 | 5/2019 | Zhou | |
| 10,307,098 B2 | 6/2019 | Gareau | |
| 10,335,027 B2 | 7/2019 | Pamplona et al. | |
| 10,345,680 B2 | 7/2019 | Pikkula et al. | |
| 10,349,893 B2 | 7/2019 | Lee et al. | |
| D858,758 S | 9/2019 | Mulumudi et al. | |
| 10,405,752 B2 | 9/2019 | Khosravi Simchi et al. | |
| 10,438,356 B2 | 10/2019 | Dacosta | |
| 10,458,902 B2 | 10/2019 | Ast et al. | |
| 10,492,679 B2 | 12/2019 | Zhou | |
| 10,539,463 B2 | 1/2020 | Hwang et al. | |
| 10,548,575 B2 | 2/2020 | Harris et al. | |
| 10,616,457 B2 | 4/2020 | Fletcher et al. | |
| 10,667,694 B2 | 6/2020 | Khosravi Simchi et al. | |
| 10,678,120 B1 | 6/2020 | Lozano-Buhl et al. | |
| 10,738,981 B2 | 8/2020 | Kim et al. | |
| 10,743,761 B2 | 8/2020 | Myung et al. | |
| 10,779,718 B2 | 9/2020 | Meyer et al. | |
| 2007/0280677 A1 | 12/2007 | Drake et al. | |
| 2009/0203986 A1 | 8/2009 | Winnick | |
| 2012/0245422 A1 | 9/2012 | Hasbun | |
| 2012/0320340 A1 | 12/2012 | Coleman | |
| 2013/0083185 A1 | 4/2013 | Coleman | |
| 2013/0102359 A1 | 4/2013 | Ho | |
| 2013/0300919 A1* | 11/2013 | Fletcher | H04N 17/002 |
| | | | 348/360 |
| 2014/0073880 A1 | 3/2014 | Boucher et al. | |
| 2015/0002950 A1 | 1/2015 | O'Neill et al. | |
| 2015/0087926 A1 | 3/2015 | Raz et al. | |
| 2015/0172522 A1* | 6/2015 | O'Neill | H04N 23/56 |
| | | | 348/240.3 |
| 2016/0166150 A1* | 6/2016 | Vilenskii | A61B 5/0077 |
| | | | 348/77 |
| 2016/0178937 A1 | 6/2016 | Pham et al. | |
| 2016/0232389 A1 | 8/2016 | Gifford | |
| 2016/0249805 A1* | 9/2016 | Salvati | A61B 3/14 |
| | | | 351/206 |
| 2017/0007126 A1 | 1/2017 | Shahar | |
| 2017/0014024 A1 | 1/2017 | Wachs | |
| 2017/0027432 A1 | 2/2017 | Wachs | |
| 2017/0119250 A1 | 5/2017 | Kolachalama et al. | |
| 2017/0303857 A1 | 10/2017 | Perkins et al. | |
| 2017/0354380 A1 | 12/2017 | Wagstaff | |
| 2018/0055357 A1 | 3/2018 | Meyerson et al. | |
| 2018/0153399 A1 | 6/2018 | Fink et al. | |
| 2018/0160887 A1 | 6/2018 | Hefez et al. | |
| 2018/0279870 A1 | 10/2018 | Walsh et al. | |
| 2018/0303329 A1 | 10/2018 | Goldfain et al. | |
| 2018/0353073 A1 | 12/2018 | Boucher et al. | |
| 2018/0360295 A1 | 12/2018 | Boucher et al. | |
| 2019/0038135 A1* | 2/2019 | Lee | A61B 3/12 |
| 2019/0038232 A1 | 2/2019 | Mirza et al. | |
| 2019/0046168 A1* | 2/2019 | Harris | A61B 5/0077 |
| 2019/0082951 A1 | 3/2019 | Merriam et al. | |
| 2019/0090751 A1 | 3/2019 | Hwang et al. | |
| 2019/0099615 A1 | 4/2019 | Higgins et al. | |
| 2019/0125249 A1 | 5/2019 | Rattner et al. | |
| 2019/0133435 A1 | 5/2019 | Browne et al. | |
| 2019/0133514 A1 | 5/2019 | Gareau et al. | |
| 2019/0133515 A1 | 5/2019 | Park et al. | |
| 2019/0200931 A1 | 7/2019 | Geva | |
| 2019/0216402 A1* | 7/2019 | Sayani | A61B 1/233 |
| 2019/0239729 A1 | 8/2019 | Lim et al. | |
| 2019/0239797 A1 | 8/2019 | Tsang et al. | |
| 2019/0246986 A1 | 8/2019 | Rodger et al. | |
| 2019/0247009 A1 | 8/2019 | Mulumudi et al. | |
| 2019/0274619 A1 | 9/2019 | Gareau et al. | |
| 2019/0328224 A1 | 10/2019 | Nevin | |
| 2019/0331982 A1 | 10/2019 | Pikkula et al. | |
| 2020/0015832 A1 | 1/2020 | Levine et al. | |
| 2020/0036874 A1 | 1/2020 | Barros et al. | |
| 2020/0080942 A1 | 3/2020 | Chen et al. | |
| 2020/0094030 A1 | 3/2020 | Kim et al. | |
| 2020/0104998 A1 | 4/2020 | Dacosta | |
| 2020/0113499 A1 | 4/2020 | Schreiber et al. | |
| 2020/0121190 A1 | 4/2020 | Whitehead | |
| 2020/0121243 A1 | 4/2020 | Anderson et al. | |
| 2020/0163622 A1 | 5/2020 | Geva et al. | |
| 2020/0178776 A1 | 6/2020 | Kwong | |
| 2020/0237310 A1 | 7/2020 | Lozano-Buhl et al. | |
| 2020/0281534 A1 | 9/2020 | Geva et al. | |
| 2021/0191457 A1* | 6/2021 | Thorsten Heiko Schelske | |
| | | | G01J 3/522 |
| 2021/0259625 A1* | 8/2021 | Saiko | A61B 5/445 |

* cited by examiner

40

USER DEVICE

PROCESSOR 42     44

MEMORY

INSTRUCTIONS

46

COMMUNICATION MODULE 48     49

I/O PORTS

FIG. 21

REMOTE MEDICAL EXAMINATION

CROSS REFERENCE TO RELATED APPLICATIONS

The present application is a continuation of U.S. Non-provisional patent application Ser. No. 17/453,169, filed Nov. 1, 2021, which claims priority to and the benefit of U.S. Provisional Patent Application No. 63/198,668, entitled "REMOTE MEDICAL EXAMINATION," filed Nov. 2, 2020, which is incorporated by reference as if fully set forth below and for all applicable purposes.

TECHNICAL FIELD

The present disclosure relates generally to remote medical examinations (e.g., telemedicine) and, in particular, to systems and devices for remote ear, nose, and throat (ENT) examination.

INTRODUCTION

Telemedicine, or virtual medicine, visits may provide several benefits to both patients and physicians. For instance, a patient may use a call or a video-conference with a doctor as a convenient alternative in terms of time and/or cost to an in-person visit to a clinic. Moreover, by receiving care at home, the patient may reduce the risk of spreading or contracting an infectious disease within the clinic. To that end, a physician or care-provider's risk of contracting an infectious disease while examining a patient may also be reduced with increased use of telemedicine. Yet, the use of telemedicine remains constrained in fields of medicine that rely on more intensive examination procedures, such as ear, nose, and throat (ENT) practices. For example, to examine an ear, nose, and/or throat a physician may use an otoscope, one or more speculums, and/or a tongue depressor. In other words, while examining a patient, the physician may use a set of tools to light, gain access to, and/or magnify anatomical features. However, use of these tools may be cumbersome and/or inadequate for use in the telemedicine context. Thus, the use of telemedicine visits is restricted by a limited access to and usability of at-home examination devices for both patients and physicians, alike.

SUMMARY

Embodiments of the present disclosure relate to systems and devices for facilitating remote (e.g., virtual) medical examination of a patient. More specifically, the present disclosure relates to a remote exam attachment that, along with a user device, may be be used to capture images of an anatomical feature for examination of a patient. For instance, the remote exam attachment may include a magnifying lens, which may magnify an image of an object obtained at a camera of the user device. The remote exam attachment may also couple to an examination tool, such as a speculum, a scope, a tongue depressor, and/or the like, which may provide access to and/or further magnification of the anatomical feature. Further, the remote exam attachment may couple to an external light attachment, which may illuminate the anatomical feature such that a user (e.g., a physician) may distinguish aspects of the anatomical feature and/or diagnose a condition associated with the anatomical feature. Moreover, the user device may be configured to adjust one or more settings of the camera, such as the zoom, field of view, aperture, and/or the like, to interface with the remote exam attachment. The user device may be configured to adjust these settings automatically, in response to detecting a condition (e.g., an image feature, such as the focus of the image), and/or in response to a user input. The user input may be received directly at the user device from a first user, such as a patient, and/or remotely from a second user, such as a physician. The user device may further be configured to transmit an image captured in conjunction with the remote exam attachment to another user device, which may be associated with another user (e.g., a physician). Accordingly, the remote exam attachment, in conjunction with the user device, may capture, display, and/or transmit images of an anatomical feature. In this way, the remote exam attachment, along with the user device, may be used to perform a remote examination of a patient, which may include an examination performed by the patient himself.

In some aspects, a remote medical examination system comprises: a remote exam attachment operable to removably couple to a user device, the remote exam attachment comprising a lens and a flange; and an external light attachment coupled to the remote exam attachment, the external light attachment comprising: a light source; and a window, wherein the window is aligned with the lens such that light passes from the window through the lens. The external light attachment may be operable to removably couple to the remote exam attachment at the flange. In some instances, the external light attachment is fixedly coupled to the remote exam attachment. In some instances, the remote exam attachment further comprises a clip, and the remote exam attachment is operable to removably couple to the user device via the clip. In some aspects, the remote exam attachment further comprises an arm and a support coupled to the arm, wherein the arm and the support are operable to removably couple with a tongue depressor. In some instances, the external light attachment further comprises an additional flange. A speculum may be operable to removably couple to the remote exam attachment at the flange or to the external light attachment at the additional flange. The speculum may be sized and shaped for use with at least one of an ear or a nose of a patient. In some instances, the remote exam attachment is sized and shaped such that the lens is optically aligned with a camera lens of the user device when the remote exam attachment is coupled to the user device. The camera lens may be a front-facing camera or a rear-facing camera of the user device.

In some aspects, a method of remote medical examination comprises: coupling a remote exam attachment to a user device; positioning, with the remote exam attachment coupled to the user device, a portion of the remote exam attachment in proximity to an orifice of a patient such that a camera of the user device is oriented to capture an image of a region of interest within the orifice; and obtaining, with the portion of the remote exam attachment in proximity to the orifice of the patient, one or more images of the region of interest with the camera of the user device. The camera of the user device may be a front-facing camera or a rear-facing camera. In some instances, the positioning the portion of the remote exam attachment in proximity to the orifice of the patient and the obtaining the one or more images of the region of interest with the camera of the user device are performed by the patient. The method may further comprise determining, by the patient, that the camera of the user device is oriented to capture the image of the region of interest within the orifice based on display of the user device. In some instances, the determining that the camera of the user device is oriented to capture the image of the region of interest within the orifice based on display of the user device comprises viewing a reflection of the display in a reflective surface. In some instances, the portion of the remote exam attachment comprises at least part of a tongue depressor. The orifice of the patient may be a mouth of the patient. In some instances, the portion of the remote exam attachment comprises at least part of a speculum. The orifice of the patient may be at least one of an ear or a nose of the patient.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

Figure 21:
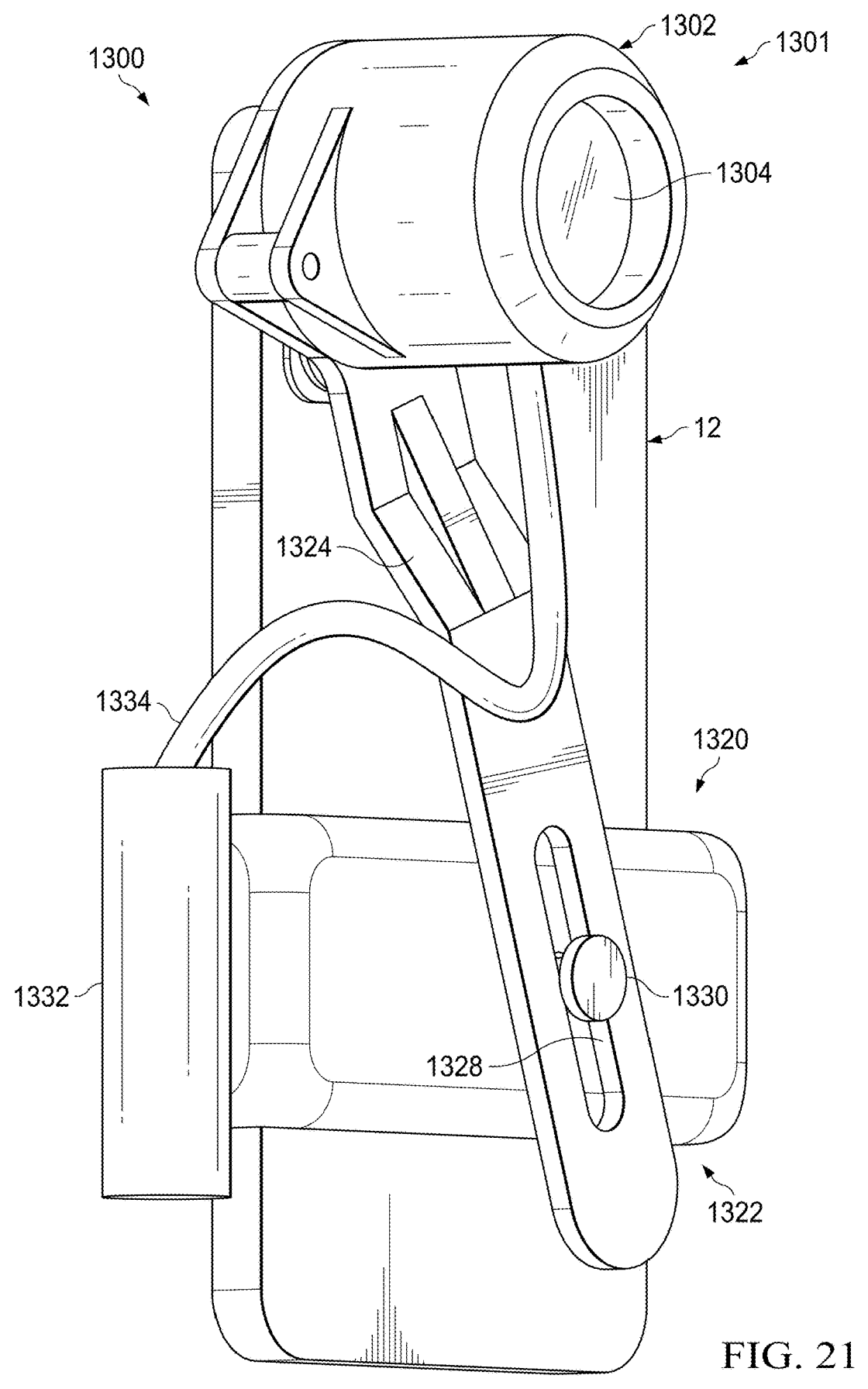

FIG. 21 is a perspective view of a remote exam system, according to embodiments of the present disclosure.

DETAILED DESCRIPTION

Figure 1:
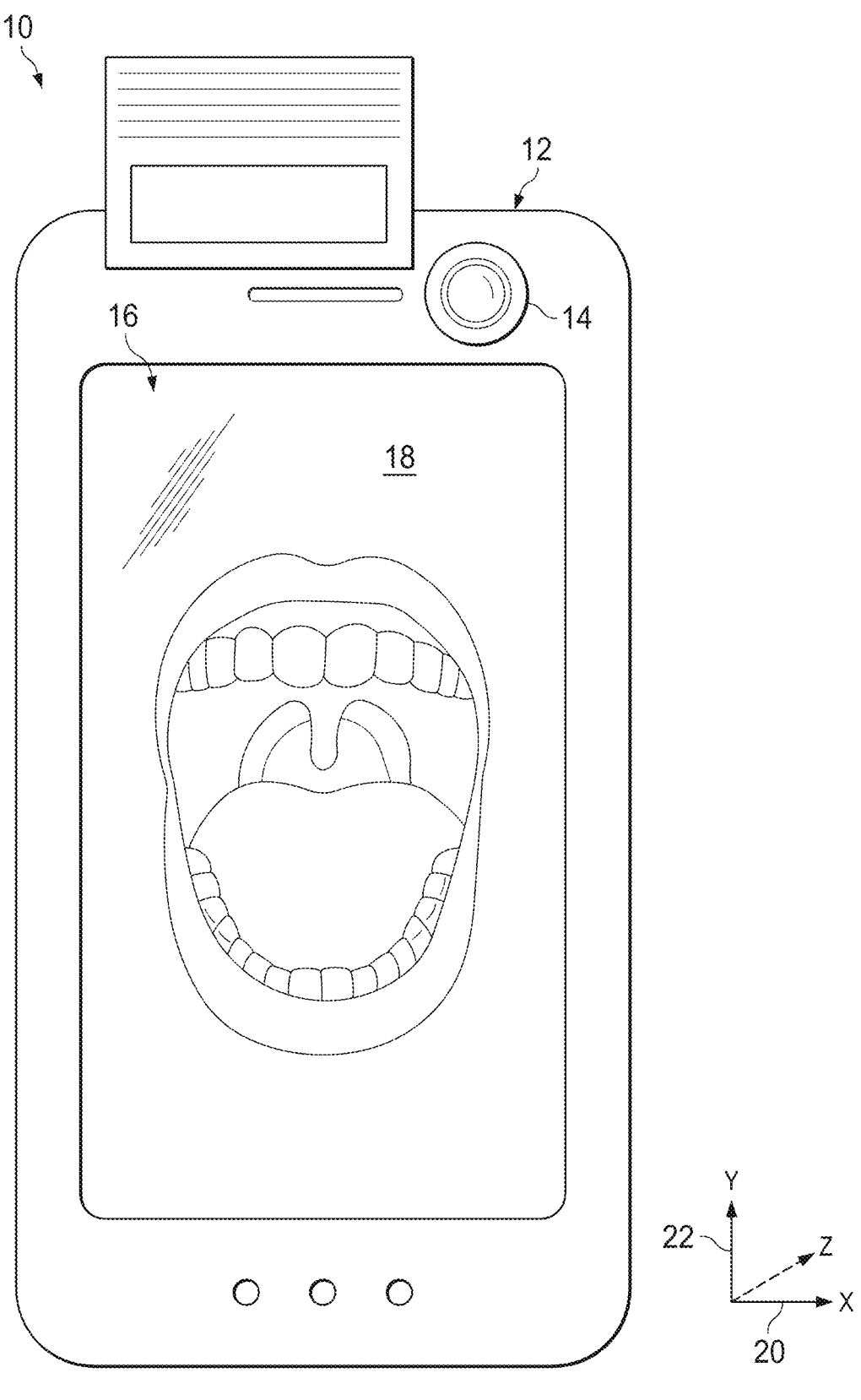
FIG. 1 is a schematic diagram of a front view of a remote exam attachment coupled to a user device, according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure relates to systems and devices for facilitating remote (e.g., virtual) medical examination of a patient. More specifically, the present disclosure relates to at-home examination (e.g., self-examination) of the ear, nose, and/or throat (ENT), among other anatomical features. In some embodiments, for example, a remote exam attachment may removably couple to a user device that includes a camera, such as a phone, computer, or tablet, so that the remote exam attachment interfaces with the camera. The remote exam attachment may also include a magnifying lens. Accordingly, when attached to the user device, the remote exam attachment provides additional magnification to the camera of the user device. Moreover, the remote exam attachment may removably couple to a set of speculums and/or scopes that, when attached to the remote exam attachment, align with the lens. To that end, when both the remote exam attachment and a corresponding speculum are attached together at the user device, the camera of the user device may capture images similar to those captured by an endoscopic device, such as an otoscope.

In some embodiments, the set of speculums and/or scopes may include a speculum suitable for examining a patient's nose, which may be rigid or flexible, as well as a speculum suitable for examining a patient's ear. A tongue depressor may further removably couple to the remote exam attachment and may be used in oral examinations. Thus, the images captured by the camera with the remote exam attachment and a speculum and/or tongue depressor coupled together at the user device, may be used by a physician to, remotely or in-person, examine an ear, the nose, and/or the throat of a patient. As such, the capabilities of an ENT specialist may be extended to scenarios where the ENT may otherwise be unavailable. For example, using the techniques described herein, the ENT specialist may provide services (e.g., examination services, diagnostic services, and/or the like) to a hospital, clinic, and/or patient that otherwise lack access to the services of an ENT specialist. That is, for example, the ENT specialist may provide services to remote locations, such as a rural location and/or a patient's location during travel, and/or the ENT specialist may provide services to hospitals and/or clinics that are unable to staff an ENT specialist (e.g., due to expense, availability, and/or the like).

In some embodiments, the patient may use the remote exam attachment independently to capture an image of an anatomical feature and subsequently transmit the image to a physician at a later time. Additionally, or alternatively, the patient may capture and share the image in real-time during a telemedicine visit with the physician. For instance, in such embodiments, the patient and the physician may video conference, which may allow the physician to view images while they are being captured by the patient using a first user device. By video-conferencing, the physician may provide instruction to the patient regarding use of the remote exam attachment, use of the speculums, images needed for the examination, how to best capture these images (e.g., positioning of the remote exam attachment), and/or the like. Further, in some embodiments, the physician may be provided with additional control over the examination of the patient via a user device used by the physician (e.g., a second user device). For instance, while conducting the telemedicine visit, the physician may be able to control one or more settings of the patient's user device (e.g., the first user device) via the second user device. In some embodiments, for example, the second user device may be configured to control the camera at the first user device to adjust the zoom, aperture, field of view of an image and/or to capture and record an image. Moreover, to interface with the remote exam attachment, the first user device may be configured to automatically adjust one or more settings of the camera and/or other components of the first user device. To that end, the first user device may be configured to turn on the flash, simultaneously capture images with multiple cameras, such as a front and a rear-facing camera, adjust a zoom or camera setting based on a lens and/or a speculum attached to the remote exam attachment, and/or the like, as discussed in greater detail below.

Figure 3:
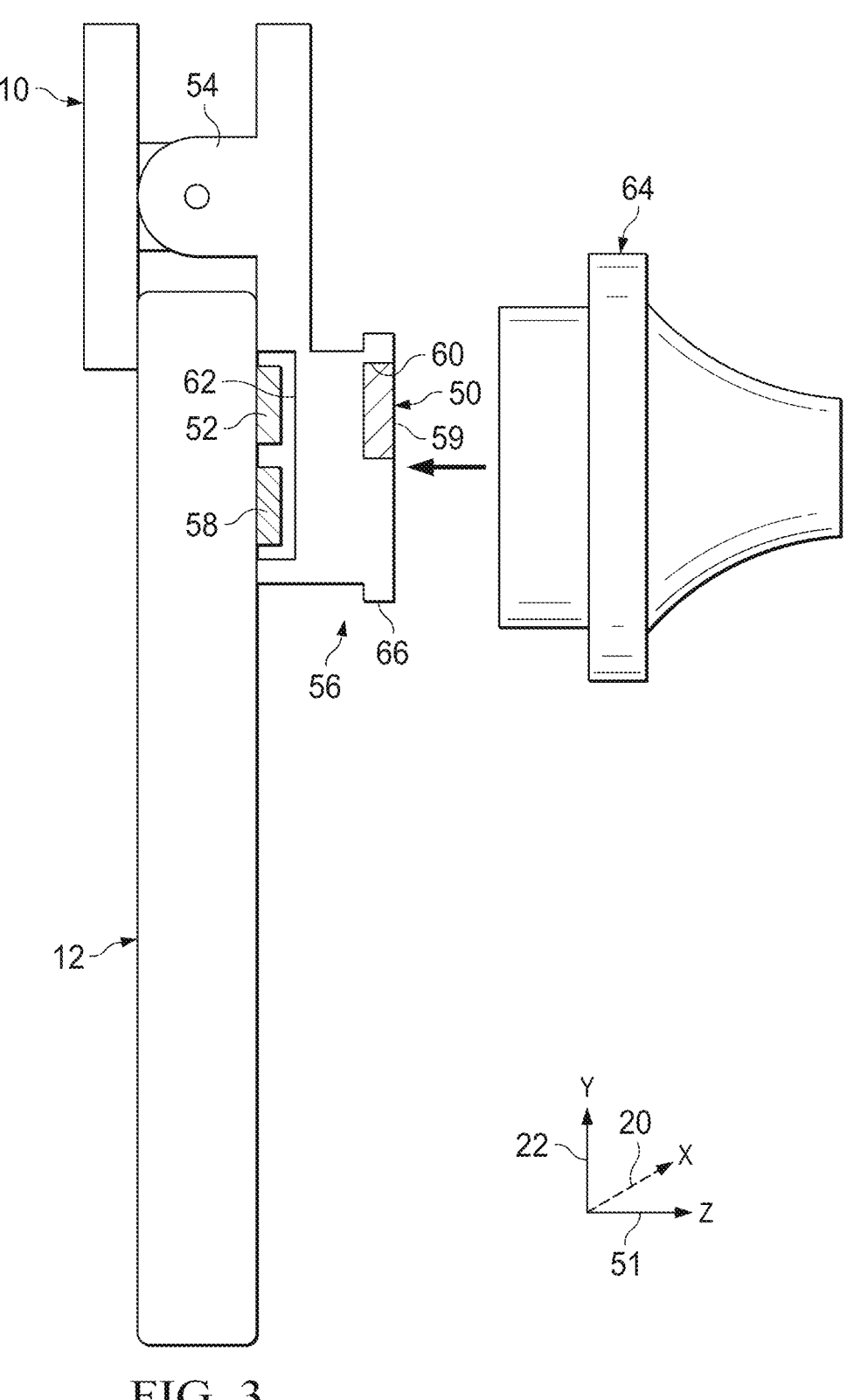
FIG. 3 is a schematic diagram of a side view of a remote exam attachment, a user device, and a speculum, according to embodiments of the present disclosure.

FIG. 1 illustrates a schematic diagram of a front view (corresponding to a plane with respect to an x-axis 20 and a y-axis 22) of an embodiment of a remote exam attachment 10 coupled to a user device 12. As illustrated, the remote exam attachment 10 may be implemented as a clip, such as a spring-loaded clip, that may removably attach to the user device 12. In other embodiments, the remote exam attachment 10 may attach to the user device 12 or a case coupled to the user device 12 via magnets, a clamping mechanism, a suction cup, and/or a screw-on mechanism. Further, the remote exam attachment 10 may be included in a case formed to snap-fit onto the user device 12. In any case, the remote exam attachment 10 may be implemented to couple to the user device 12 so that a portion of the remote exam attachment 10, such as a lens, is aligned with a camera of the user device 12, as illustrated in FIG. 3. To that end, the user device 12 may correspond to any suitable device that includes a camera, such as a mobile phone, a tablet, a laptop computer, and/or the like. Moreover, while embodiments described herein relate to aligning the remote exam attachment 10 with a rear-facing camera of the user device, embodiments are not limited thereto. Accordingly, in some embodiments, the remote exam attachment 10 may be utilized in conjunction with a front-facing camera, such as front-facing camera 14.

By interfacing the remote exam attachment 10 with a camera of the user device 12, the user device 12 may be used to capture images or videos suitable for use in medical examinations and/or for making a diagnosis. For instance, the remote exam attachment 10 may enable the camera to capture an image with a magnification, resolution, field of view, and/or the like suitable to capture details of an anatomical feature for examination by a physician (e.g., a user). In particular, the remote exam attachment 10 may be used, along with the user device 12, to examine and/or capture photos of a dermatological feature (e.g., a mole, cut, burn, and/or the like), an eye, an ear, a nose, a throat, and/or the like. Further, the remote exam attachment 10 may couple to one or more examination tools, such as a scope, speculum, and/or a tongue depressor, which may provide access to an anatomical feature, such as an ear, nose, or throat for imaging and examination, as described in greater detail below. To that end, the user device 12 may correspond to a device used by a physician to examine a patient in-person or a device used by a patient to perform an at-home examination with or without the assistance of a third party, for example. Accordingly, in some embodiments, the user device 12 may be implemented to capture, display, and transmit images taken in conjunction with the remote exam attachment 10 to another device, such as another user device.

As illustrated, in some embodiments, the user device 12 may be implemented to provide a graphical user interface (GUI) 16, or application, for use during an examination. The GUI 16 may be configured to assist a user, such as a patient or physician, during the examination. For instance, the GUI 16 may be configured to provide an output, such as a set of visual signals, audio signals, and/or signals configured to cause the user device to vibrate, during the examination. In particular, the user device 12 may output, at the GUI 16, an image captured by the camera of the user device 12 in conjunction with the remote exam attachment 10. The image output to the GUI 16 may be provided at a display 18, as illustrated. In some embodiments, the GUI 16 may be configured to display images captured by the camera in full-screen (e.g., within a majority of the area of the display 18). As such, the GUI 16 and/or the user device 12 may be configured to control the field-of-view of the camera, the zoom settings of the camera, and/or the like to ensure an image captured by the camera will fill a certain area of the display 18. Additionally, or alternatively, the user device 12 may be configured to process an image received from the camera by, for example, cropping or zooming in on the image prior to displaying the image at the GUI 16.

The user device 12 may be configured to receive and/or detect one or more inputs at the GUI 16. For instance, the GUI 16 may be configured to receive a user input via an input device (e.g., a sensor, button, touch-screen, microphone, and/or the like) coupled to the user device 12 or via an input transmitted to the user device 12 from another device, such as another user device. In this way, the input may correspond to an input provided by a patient at the user device 12 (e.g., via a first user) or an input provided by a physician (e.g., a second user) at another device communicatively coupled to the user device 12 (e.g., via a teleconference or a videoconference). To that end, a user may control the user device 12 at the user device 12 itself and/or via a remote connection with the user device 12. Thus, a physician may remotely adjust the camera or another component of the user device 12 while a patient positions the user device 12 for examination of an anatomical feature, for example. Additionally, or alternatively, an input at the GUI 16 may correspond to a condition automatically detected by the user device 12. In any case, the user device 12 may be configured to provide an output, via the GUI 16, in response to receiving or detecting the one or more inputs. For instance, to output the image described above, the user device 12 and/or the GUI 16 may be configured to detect a percentage and/or an area of the display 18 that the image will occupy and may determine, based on the percentage and/or the area, whether to adjust (e.g., zoom-in, crop, expand, and/or the like) the image for display.

Further, in some aspects, the user device 12 may be configured, via the GUI 16, to control a flash, or light element, of the user device 12. For instance, the GUI 16 may maintain the flash powered fully on and/or powered to provide a certain luminosity. Accordingly, the GUI 16 may ensure that an object imaged at the camera of the user device 12 is illuminated (e.g., by the light provided by the flash). In some embodiments, the GUI 16 may be configured to maintain the flash powered on throughout use of the GUI 16 and/or throughout an examination, in response to determining the remote exam attachment 10 is coupled to the user device 12, and/or in response to determining an image captured at the camera lacks a level of brightness, contrast, saturation, and/or the like. Moreover, the GUI 16 may be configured via one or more user settings, which may be input at the user device 12.

In some embodiments, the GUI 16 may be configured to use multiple cameras of the user device 12. For instance, the GUI 16 may be configured to use a front-facing camera of the user device 12 so that a physician may view and talk with a patient holding the user device 12 and may switch to the rear-facing camera during examination of an anatomical feature of the patient. Because the user device 12 may transmit images in real-time to a device communicatively coupled to the user device 12, use of the rear-facing camera may enable the physician to view images captured in conjunction with the remote exam attachment 10 as the patient obtains them. That is, for example, the patient and the physician may simultaneously view an image as it is being captured at the user device 12. Further, the GUI 16 and the user device 12 may be configured to capture images using multiple cameras simultaneously. In particular, the GUI 16 may be configured to use both a front-facing and a rear-facing camera of the user device 12. In such embodiments, a first image may be captured by the front-facing camera in a first direction, and a second image may be captured by the rear-facing camera in a different, second direction.

Figure 2:
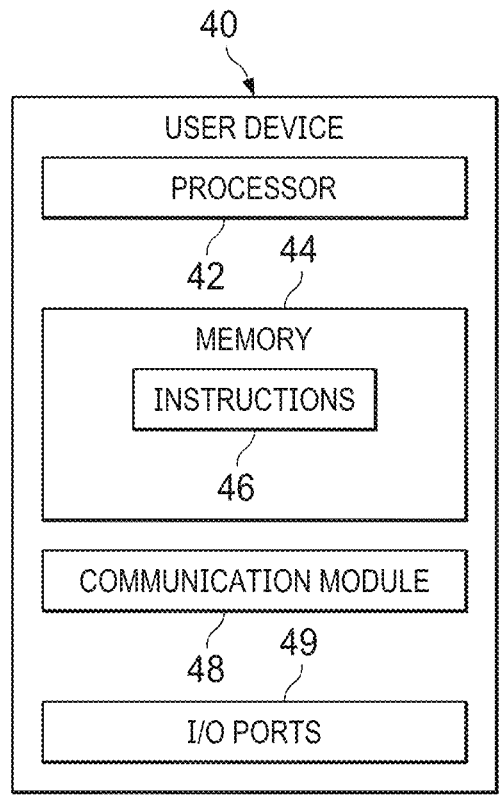
FIG. 2 is a block diagram of a user device, according to embodiments of the present disclosure.

FIG. 2 is a block diagram of an exemplary user device 40, according to aspects of the present disclosure. The user device 40 may be user device 12, as discussed with respect to FIGS. 1, 3-5, and 11. One or more user devices 40 can be configured to perform the operations described herein. The user device 40 can include additional circuitry or electronic components, such as those described herein. As shown, the user device 40 may include a processor 42, a memory 44, a communication module 48, and an input/output (I/O) port 49. These elements may be in direct or indirect communication with each other, for example via one or more buses.

The processor 42 may include a central processing unit (CPU), a digital signal processor (DSP), an application specific integrated circuit (ASIC), a controller, a field programmable gate array (FPGA) device, another hardware device, a firmware device, or any combination thereof configured to perform the operations described herein. The processor 42 may also be implemented as a combination of computing devices, e.g., a combination of a DSP and a microprocessor, a plurality of microprocessors, one or more microprocessors in conjunction with a DSP core, or any other such configuration.

The memory 44 may include a cache memory (e.g., a cache memory of the processor 42), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 44 includes a non-transitory computer-readable medium. The memory 44 may store instructions 46. The instructions 46 may include instructions that, when executed by the processor 42, cause the processor 42 to perform the operations described herein. For instance, the instructions 46 may correspond to the GUI 16 run and/or output by the user device 12, as described herein. Instructions 46 may also be referred to as code. The terms "instructions" and "code" should be interpreted broadly to include any type of computer-readable statement (s). For example, the terms "instructions" and "code" may refer to one or more programs, routines, sub-routines, functions, procedures, etc. "Instructions" and "code" may include a single computer-readable statement or many computer-readable statements.

The communication module 48 can include any electronic circuitry and/or logic circuitry to facilitate direct or indirect communication of data between the user device 40 and an additional user device, between the user device 40 and the remote exam attachment 10, and/or the like. For instance, the communication module 48 may facilitate wireless and/or wired communication between various elements of the user device 40, between the user device 40 and the additional user device, and/or between the user device and the remote exam attachment 10 using any suitable communication technology, such as a cable interface such as a USB, micro USB, Lightning, or FireWire interface, Bluetooth, Wi-Fi, ZigBee, Li-Fi, or cellular data connections such as 2G/GSM, 3G/UMTS, 4G/LTE/WiMax, or 5G. Accordingly, the communication module 48 may include one or more transceivers, antennae, and/or the like.

The user device 40 may also include one or more I/O ports 49, which may couple the user device 40 to an I/O device. For instance, the I/O ports 49 may couple the user device 40 to an input device, such as a camera (e.g., camera 14), touch sensitive pad, touch screen display (e.g., display 18), keyboard, mouse, microphone, trackpad, button, scroll wheel, and/or the like. The I/O ports 49 may further couple the user device 40 to an output device, such as a speaker, display (e.g., display 18), light (e.g., flash), and/or the like. The input device and/or the output device may be integrally formed with the user device 40 or may be separate from the user device 40. In some instances, an I/O device may removably couple to the user device 40 at the I/O ports 49.

Turning now to FIG. 3, a schematic diagram of a side view (corresponding to a plane with respect to a z-axis 51 and a y-axis 22) of the remote exam attachment 10 and the user device 12 is illustrated, in accordance with an embodiment. As illustrated, the remote exam attachment 10 may include a clip 54 to couple the remote exam attachment 10 to the user device 12 and may include an imaging assembly 56, which may interface with the camera 52 of the user device 12, a flash 58 (e.g., a light) of the user device 12, or both. More specifically, the imaging assembly 56 may be shaped to fit over the camera 52 and/or the flash 58 when the remote exam attachment 10 is coupled to the user device 12. For instance, the imaging assembly 56 may be sized to surround the camera 52 and/or flash 58 and may be configured for flush positioning or positioning within a certain distance of the camera 52 and/or the flash 58 when the remote exam attachment 10 is coupled to the user device 12.

In addition, the imaging assembly 56 may be formed so that light travelling from an object, such as an anatomical feature, to the camera 52 may pass through a first face 59 of the imaging assembly 56 and be received at the camera 52 via a second face 62 of the imaging assembly. Moreover, the imaging assembly 56 may include a lens 50 aligned with the camera 52 and positioned between the first face 59 and the second face 62. In some embodiments, the lens 50 may be configured to provide magnification (e.g., 1.5×, 2×, 3×, 5×, 6× magnification, and/or the like) to an image captured at the camera 52. For instance, the lens 50 may be a macro lens, a telephoto lens, and/or the like. In this way, the user device 12 may obtain more detailed images of an anatomical feature. Additionally, or alternatively, the lens 50 may be configured to alter the field-of-view of the camera 52. In some embodiments, for example, the lens 50 may be a fish eye lens, which may provide wider angles of view for images captured at the user device 12.

Moreover, the imaging assembly 56 and the lens 50 may be implemented so that different lenses may be interchanged for use with the camera 52. To that end, the imaging assembly 56 may include a plurality of lenses that may be rotated or slid from an inactive position out of alignment with the camera 52 to an active position suitable for use with the camera 52. For instance, the illustrated lens 50 may represent a lens in the active position for use with the camera 52, while additional lenses are positioned elsewhere within the imaging assembly. In other embodiments, the imaging assembly 56 may include a lens housing 60 constructed so that different lenses may removably couple with the lens housing 60. In such embodiments, a first lens (e.g., lens 50) may screw, slide, snap-fit, or pressure-fit into the lens housing 60 and may later be removed from the housing such that a second lens may be positioned within the lens housing 60. Accordingly, any suitable lens may be included within the imaging assembly 56 or configured to interface with the imaging assembly 56 (e.g., at the lens housing 60). Further, in some embodiments, the GUI 16 (FIG. 1) may be configured to detect or receive an input indicating the lens actively used by the remote exam attachment 10. In such cases, the GUI 16 may adjust an image captured at the camera 52 based on the active lens.

While the remote exam attachment 10 is described herein as interfacing (e.g., via the lens 50) with the camera 52, it may be appreciated that the remote exam attachment 10 may interface with multiple cameras simultaneously. In particular, the remote exam attachment 10 may focus, via one or more lenses, light from an object on one or more cameras of the user device 12 so that the user device 12 may capture an image of the object. To that end, embodiments described herein are intended to be illustrative and not limiting.

As further illustrated, the remote exam attachment 10 may couple to a speculum 64 (e.g., an examination tool). In particular, the speculum 64 may correspond to a speculum sized and shaped to fit within an ear canal and/or a nasal passage, as better illustrated in FIGS. 6A-6B, 7A-7B, 8A-8B, and 9. Additionally or alternatively, the speculum 64 may be a flexible scope, which may be flexed in one or more directions to navigate to a position within a cavity, such as a nasal passage. To that end, the speculum 64, along with the remote exam attachment 10, may provide access to a patient's internal anatomical features, such as an ear canal and/or a nasal passage, for imaging and/or examination via the camera 52. Additionally, or alternatively, the speculum 64 may include an additional lens. In this way, the speculum 64 may provide additional magnification (e.g., along with the lens 50) to an image of an object captured at the camera 52. Thus, in some embodiments, the remote exam attachment 10 may be used for examination of an ear or nose, among other anatomical features, when coupled with the speculum 64. Moreover, in some embodiments, the GUI 16 (FIG. 1) may be configured to detect or receive an input identifying a speculum (e.g., speculum 64) coupled to the remote exam attachment 10. In such cases, the GUI 16 may adjust an image captured at the camera 52 based on the identified speculum.

The speculum 64 and the remote exam attachment 10 may be coupled via a snap-fit connection, a pressure-fit connection, threading, magnets, and/or the like. Thus, in some embodiments, the imaging assembly 56 may include a flange 66 that may maintain a stable connection with the speculum 64, when attached, so that the speculum 64 is secured during examination of a patient. Similarly, the speculum 64 may include an annular ring or may otherwise change diameter to interface with the flange 66.

In some embodiments, light provided by the flash 58 may be sufficient to illuminate an anatomical feature for an image suitable for use in an examination to be captured by the camera 52. For instance, the light provided by the flash 58 may illuminate a patient's oral cavity well enough that a physician can distinguish features within the patient's mouth and/or throat and can make a diagnosis regarding the health of those features. In such embodiments, the imaging assembly 56 may be implemented so that light from the flash 58 may exit the imaging assembly 56 via the first face 59 from the second face 62.

In some embodiments, the light provided by the flash 58 may not be sufficient to illuminate an anatomical feature for the examination image to be captured by the camera 52. For instance, the light provided by the flash 58 may not be sufficient to light an anatomical feature, such as a nasal cavity or an ear cavity, when the remote exam attachment 10 is coupled to a speculum (e.g., speculum 64). Moreover, in some embodiments, the light provided by the flash 58 may not be sufficient to suitably illuminate an anatomical feature even when the remote exam attachment 10 is used without a speculum. Accordingly, in some embodiments, the remote exam attachment 10 may be in communication with an additional light external to the user device 12, as illustrated in FIG. 4

Figure 4:
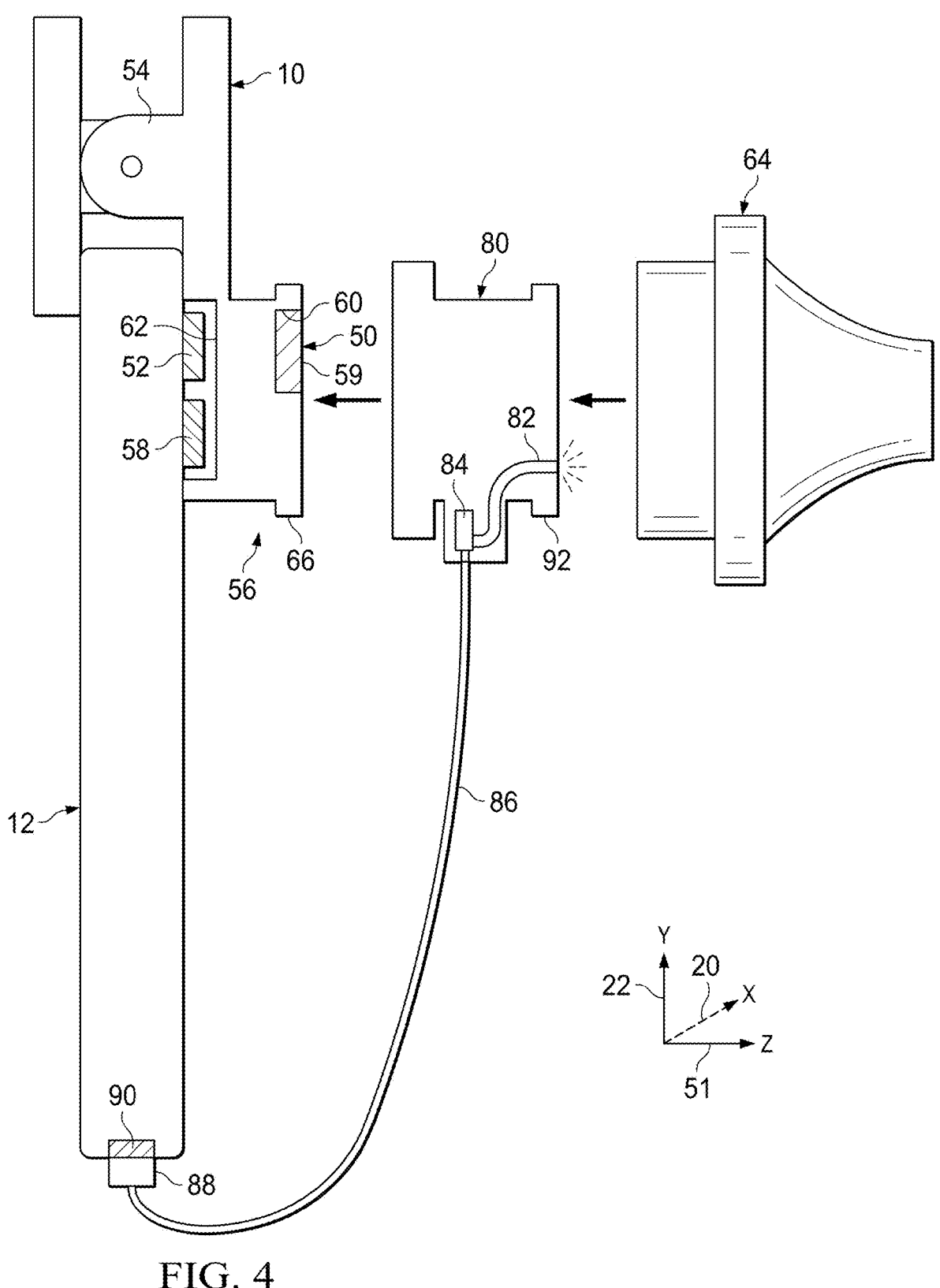
FIG. 4 is a schematic diagram of a side view of a remote exam attachment, a user device, a speculum, and an external light attachment, according to embodiments of the present disclosure.

With reference now to FIG. 4, a schematic diagram of a side view (corresponding to a plane with respect to a z-axis 51 and a y-axis 22) of the remote exam attachment 10, as well as the user device 12, the speculum 64, and an external light attachment 80 capable of interfacing with the remote exam attachment 10 is illustrated. In some embodiments, the external light attachment 80 may be used in place of the flash 58 to illuminate an anatomical feature. Accordingly, the external light attachment 80 may include a light source 82, such as a fiber optic light, a light emitting diode (LED) light, and/or the like. The light source 82 may be powered by a power source 84. In some embodiments, the power source 84 may be an internal battery, which may be replaced or recharged. Additionally or alternatively, the external light attachment 80 may be powered via a connection with a power source external to the external light attachment 80.

For instance, the external light attachment 80 may include a cable 86, which may include electrical wiring (e.g., electrical conductors), terminating in a connector 88. The connector 88 may be a lightning connector, a universal serial bus (USB) connector, an electrical plug, and/or the like. Further, by forming an electrical connection between the connector 88 and an additional power source, such as the user device 12 itself (e.g., at an electrical port 90), a wall outlet, or a battery, power may be transmitted to the external light attachment 80 via the connector 88 and the cable 86.

In some embodiments, the external light attachment 80 may additionally or alternatively supplement and/or modify the light provided by the flash 58 for illumination of an anatomical feature. For instance, in some embodiments, the light source 82 may be positioned so that, together with the flash 58, the overall intensity of light and/or total area illuminated during examination of a patient with the remote exam attachment 10 increases. Further, in some embodiments, the external light attachment 80 may include one or more lenses and/or mirrors designated to shaping (e.g., focusing) the light provided by the flash 58 to concentrate the light on a particular area.

The external light attachment 80 may couple to the remote exam attachment 10 in a similar fashion described above with reference to the speculum 64. For instance, the external light attachment 80 and the remote exam attachment 10 may be coupled via a snap-fit connection, a pressure-fit connection, threading, magnets, and/or the like. As such, the external light attachment 80 may include an annular ring or may otherwise change diameter to interface with the flange 66. Moreover, the external light attachment 80 and the speculum 64 may be coupled via a snap-fit connection, a pressure-fit connection, threading, magnets, and/or the like. Accordingly, the external light attachment may include a flange 92 that may maintain a stable connection with the speculum 64, when attached, so that the speculum 64 is secured during examination of a patient. The flange 92 and the flange 66 may be shaped and/or sized similarly so that the speculum 64 may couple directly to the remote exam attachment 10, as illustrated in FIG. 3, or to the external light attachment 80, as illustrated in FIG. 4.

Further, when coupled to the remote exam attachment 10, light from an object, such as an anatomical object, may pass through the speculum 64, the external light attachment 80, or both to reach the lens 50. The light may then continue from the lens 50 to the camera, where an image corresponding to the object may be captured.

While the remote exam attachment 10, the external light attachment 80, and the speculum 64 are illustrated and described herein as separate components, embodiments are not limited thereto. In particular, any combination of the remote exam attachment 10, the external light attachment, the speculum 64, or another suitable component may be integrally formed.

Figure 5:
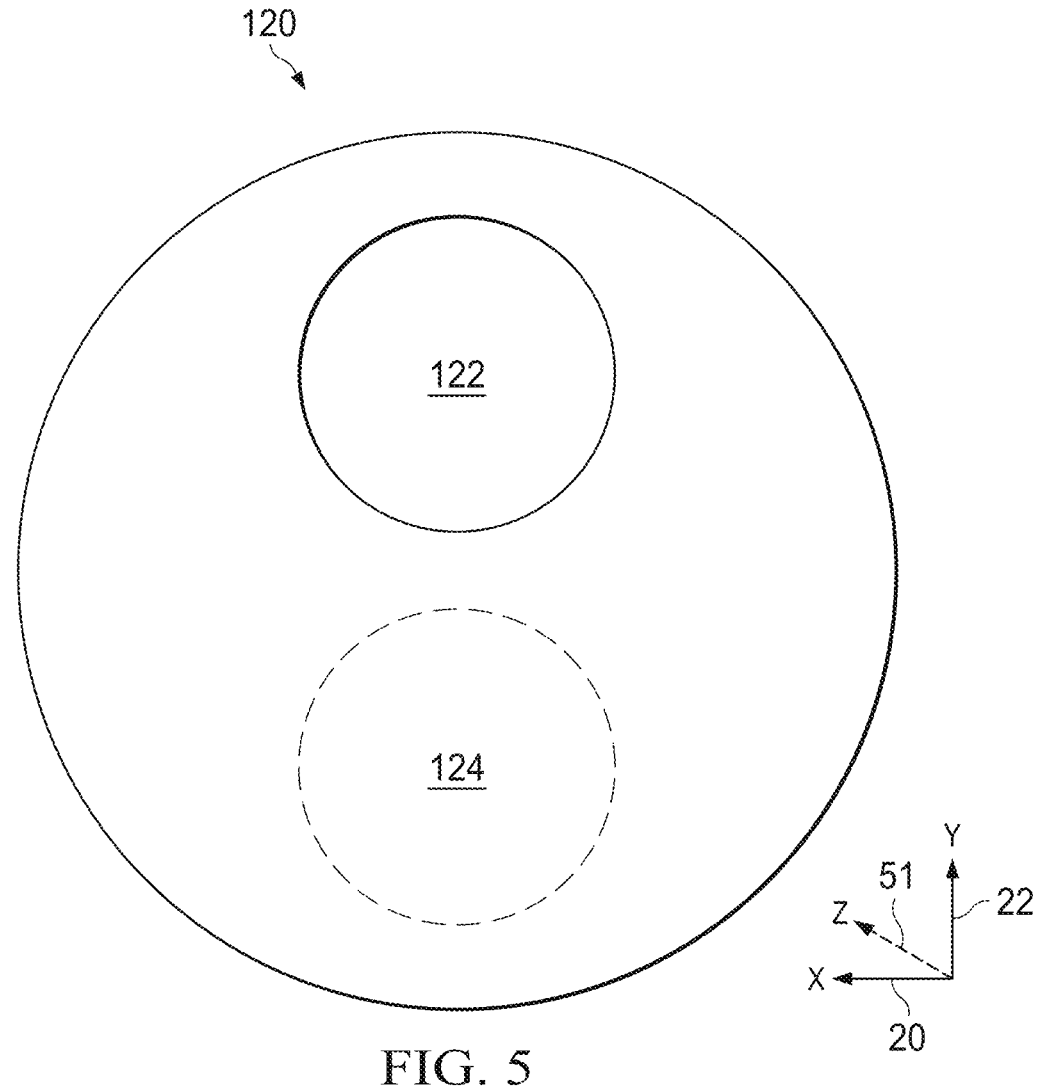
FIG. 5 is a schematic diagram of a rear view of a face of a remote exam attachment coupled to a user device, according to embodiments of the present disclosure.

FIG. 5 illustrates a schematic diagram of a rear view (corresponding to a plane with respect to the x-axis 20 and the y-axis 22) of a face 120, which may correspond to a face of the remote exam attachment 10, the external light attachment 80, or the speculum 64. As further illustrated, the face 120 may include an optical area 122, which may correspond to a lens or window, and an illumination area 124, which may correspond to an area lit by a flash (e.g., flash 58) or another light source (e.g., light source 82). More specifically, the optical area 122 may correspond to a region of the face 120 in alignment with the camera 52 of the user device 12. That is, for example, the optical area 122 may be positioned within a path travelled by light from an object to the camera

52 and associated with an image capturable at the camera 52. As an illustrative example, the face 120 may correspond to the first face 59 (FIG. 1) of the remote exam attachment 10 when coupled to the user device 12. In such cases, the optical area 122 may correspond to the area occupied by the lens 50. Further, in embodiments where the speculum 64 couples directly to the remote exam attachment 10, the light from the object may pass through an optical area 122 corresponding to the speculum 64 and then the lens 50 before reaching the camera 52. In embodiments where the speculum 64 is coupled to the external light attachment 80, which, in turn, is coupled to the remote exam attachment 10, the light may pass through the optical area 122 (e.g., a window) corresponding to the speculum 64, proceed through an optical area corresponding to the external light attachment 80 and aligned with the optical area of the speculum 64, and then pass through the lens 50 to reach the camera 52. In addition, when the external light attachment 80 is coupled to the remote exam attachment 10 without a speculum 64 coupled to either the external light attachment 80 or the remote exam attachment 10, the light may pass through the optical area of the external light attachment 80 and then pass through the lens 50 to reach the camera 52.

In the illustrated embodiment of the face 120, the optical area 122 is spaced from the illumination area 124. In some embodiments, this spacing and/or definition between the optical area 122 and the illumination area 124 may be accomplished by a wall positioned between the optical area 122 and the illumination area 124 within the remote exam attachment 10, the external light attachment 80, and/or the speculum 64. In other embodiments, the optical area 122 and the illumination area 124 may overlap or correspond to the same region within the remote exam attachment 10, the external light attachment 80, and/or the speculum 64.

Turning now to FIGS. 6-9, embodiments of speculums (e.g., scopes), such as the speculum 64, that may interface with the remote exam attachment 10 and/or the external light attachment 80 are illustrated. For instance, FIGS. 6A-B illustrate a perspective view and a schematic view of a first ear speculum 200. As illustrated, a body 202 of the first ear speculum may taper from a diameter 204 corresponding to an attachment end 206 to a diameter 208 corresponding to an examination end 210 over a length 212. In some embodiments, the attachment end 206 may couple to the remote exam attachment 10 and/or the external light attachment 80. Accordingly, the diameter 204 may be sized to engage with the remote exam attachment 10 (e.g., at flange 66) and/or the external light attachment 80 (e.g., at flange 92). In some embodiments, the diameter 204 may be approximately 24 millimeters (mm), but embodiments are not limited thereto.

Further, the examination end 210 may be sized for introduction into a patient's ear canal. Moreover, the length 212 may enable the examination end 210 to be positioned a certain distance within the ear canal. Accordingly, the length 212 and the diameter 208 may facilitate access to a patient's ear canal for imaging (e.g., at the camera 52) and/or examination. In some instances, for example, diameter 208 may be approximately 6 mm, and the length 212 may be approximately 32 mm.

Figure 6B:
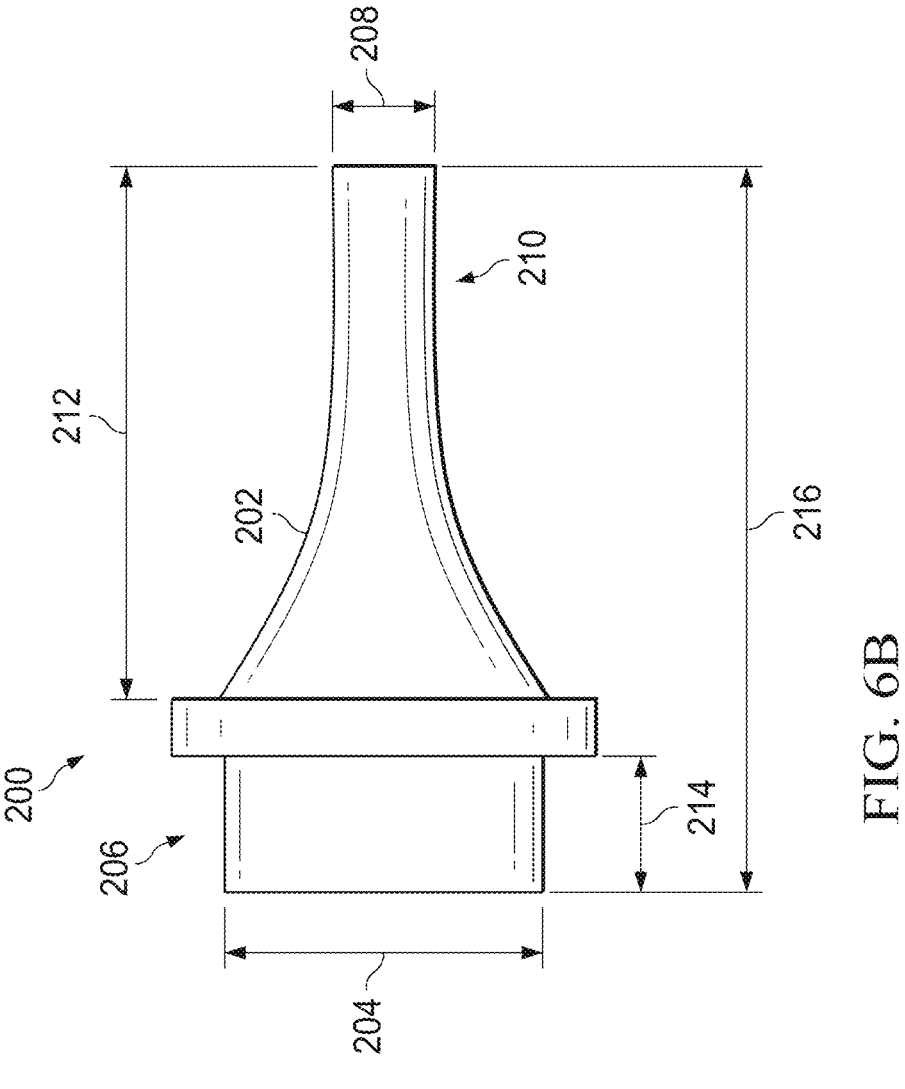
FIGS. 6A-6B illustrate a perspective view and a schematic view, respectively, of a first ear speculum, according to embodiments of the present disclosure.
Figure 6A:
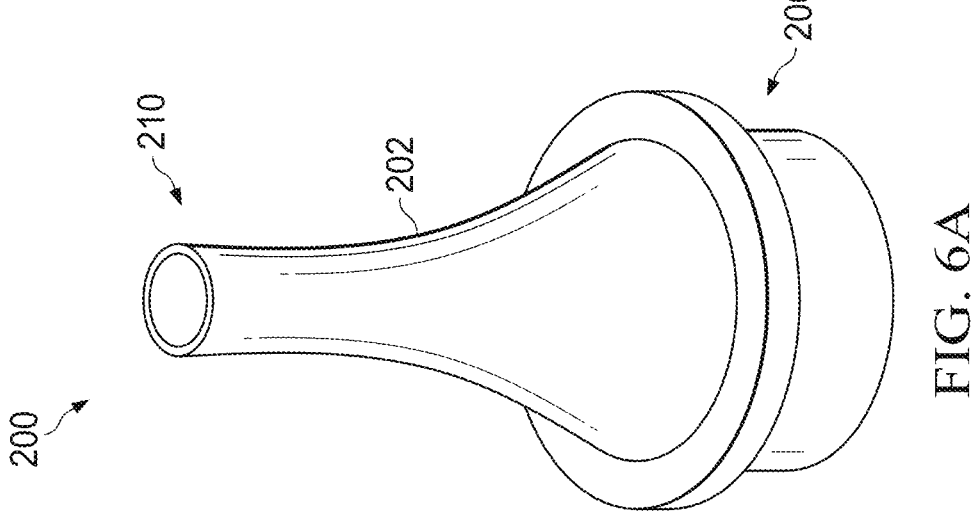

It is understood that the dimensions of the speculums may be selected for particular applications and/or uses. Referring to FIG. 6B and Table 1 (below), some exemplary dimensions for different speculum are provided. In this regard, a length 214 of the attachment end 206 in FIG. 6B corresponds to dimension a in Table 1. In some instances, the length 214 and/or the dimension a may be based on a distance from an edge of the speculum to an insertion point. In some applications, the length 214 and/or the dimension a may be between about 3.00 mm and about 15.00 mm. The length 212 of the body 202 in FIG. 6B corresponds to dimension b in Table 1. In some instances, the length 212 and/or the dimension b may be based on a distance from a beginning of a loft shape of the speculum to a minimum diameter of the speculum. In some applications, the length 212 and/or the dimension b may be between about 10.00 mm and about 40.00 mm. The diameter 208 of the examination end 210 in FIG. 6B corresponds to dimension c in Table 1. In some instances, the diameter 208 and/or the dimension c may be based on an internal diameter of a distal end of the speculum. In some applications, the diameter 208 and/or the dimension c may be between about 1.00 mm and about 15.00 mm. A length 216 of the speculum 200 in FIG. 6B corresponds to dimension d in Table 1. In some instances, the length 216 and/or the dimension d may be based on an end-to-end length of the speculum. In some applications, the length 216 and/or the dimension d may be between about 20.00 mm and about 80.00 mm. The diameter 204 of the attachment end 206 in FIG. 6B corresponds to dimension e in Table 1. In some instances, the diameter 204 and/or the dimension e may be based on an external diameter of a proximal end of the speculum. In some applications, the diameter 204 and/or the dimension e may be between about 20.00 mm and about 40.00 mm.

TABLE 1

| Speculum | a (mm) | b (mm) | c (mm) | d (mm) | e (mm) |
|---|---|---|---|---|---|
| #1 | 8.00 | 32.00 | 1.92 | 42.30 | 24.10 |
| #2 | 8.00 | 32.00 | 2.94 | 42.30 | 24.10 |
| #3 | 8.00 | 32.00 | 3.96 | 42.30 | 24.10 |
| #4 | 8.00 | 32.00 | 5.0 | 42.30 | 24.10 |
| #5 | 8.00 | 16.00 | 8.98 | 26.50 | 24.10 |

Figure 7B:
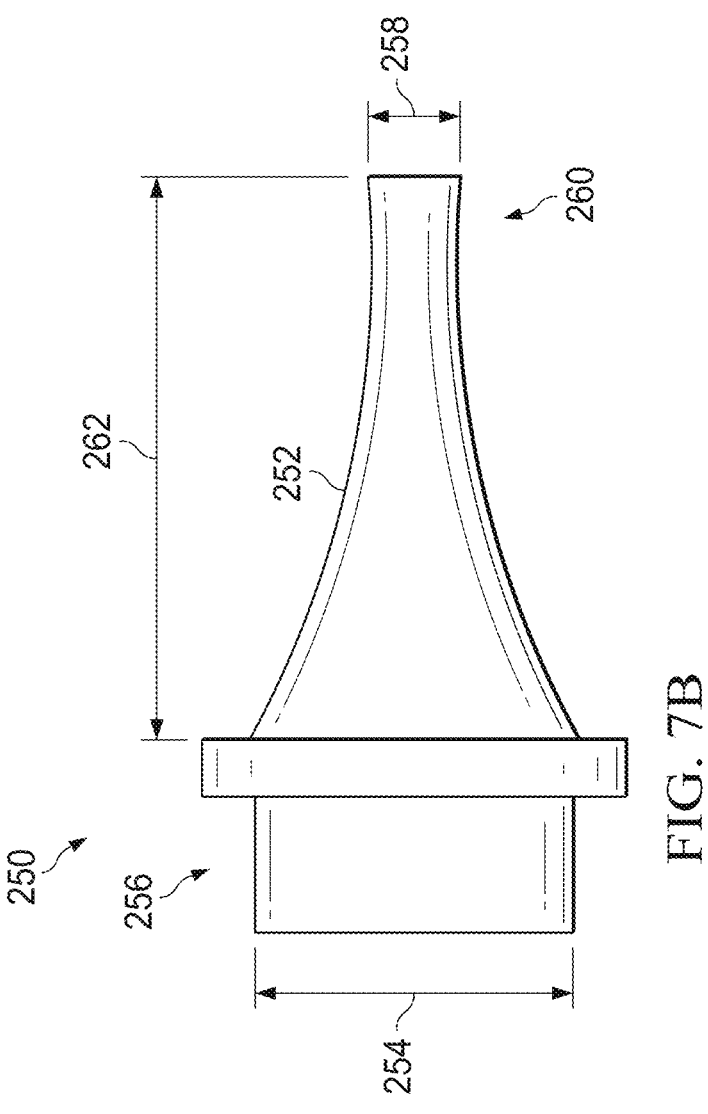
FIGS. 7A-7B illustrate a perspective view and a schematic view, respectively, of a second ear speculum, according to embodiments of the present disclosure.
Figure 7A:
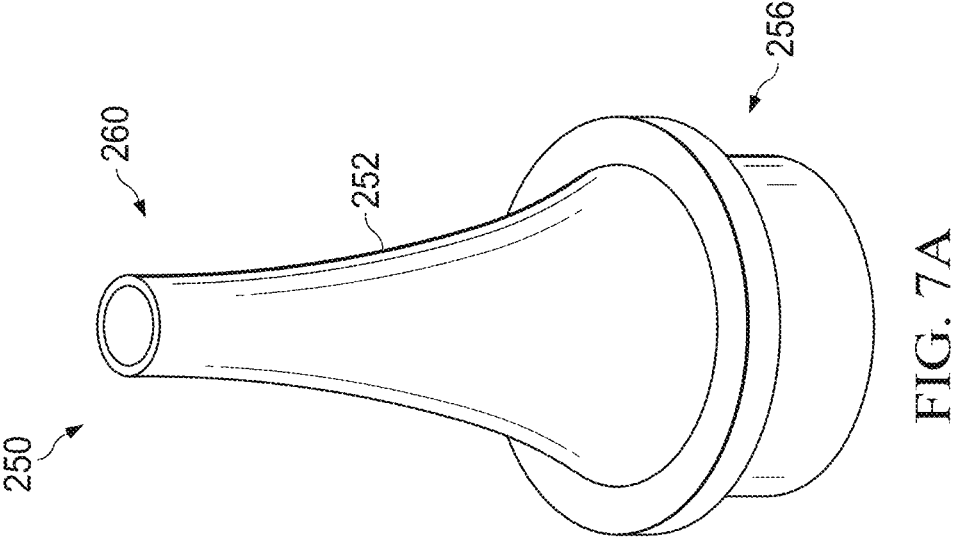

FIGS. 7A-B illustrate a perspective view and a schematic view of a second ear speculum 250. As similarly described above with reference to the first ear speculum 200, a body 252 of the second ear speculum may taper from a diameter 254 corresponding to an attachment end 256 to a diameter 258 corresponding to an examination end 260 over a length 262. In some embodiments, the diameter 254 may be the same as the diameter 204 of FIG. 6B, as the attachment end 256 may couple to the remote exam attachment 10 and/or the external light attachment 80. On the other hand, the diameter 258 of the examination end 260 and/or the length 262 may vary from the diameter 208 and the length 212, respectively. More specifically, in some embodiments, the first ear speculum 200 may correspond to a large ear speculum, while the second ear speculum 250 may correspond to a small ear speculum. That is, for example, the first ear speculum 200 may be suitable for examination of ear canals, such as an adult patient's ear canal, with a relatively larger diameter (e.g., greater than 6 mm), while the second ear speculum 250 may be suitable for examination of ear canals, such as a child patient's ear canal, with a relatively smaller diameter (e.g., less than 6 mm). In some instances, for example, the diameter 258 may be approximately 4 mm.

Figure 8B:
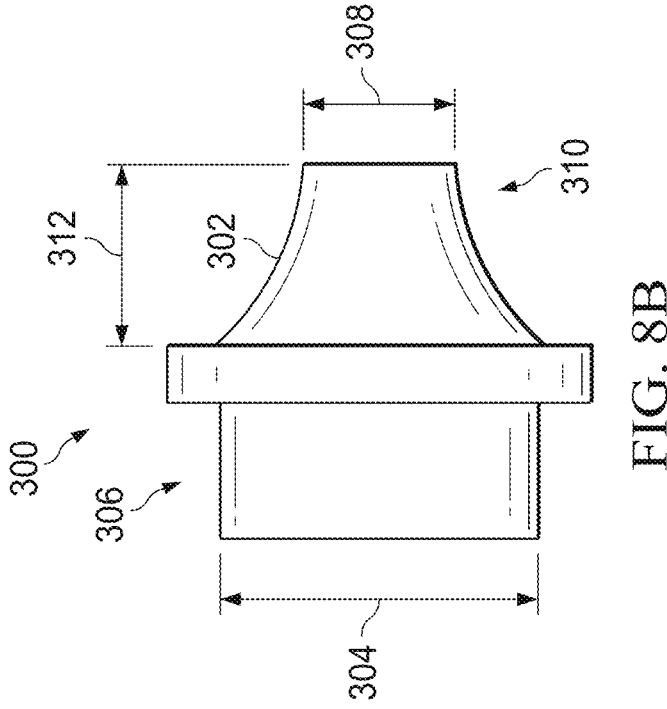
FIGS. 8A-8B illustrate a perspective view and a schematic view, respectively, of a nasal speculum, according to embodiments of the present disclosure.
Figure 8A:
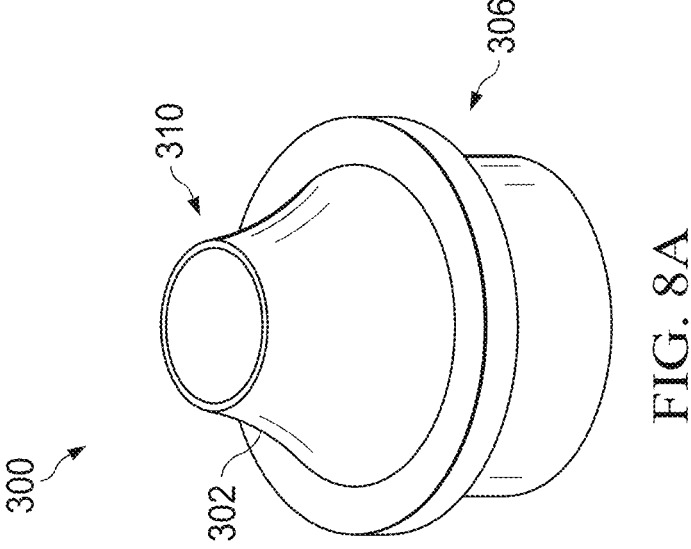

FIGS. 8A-B illustrate a perspective view and a schematic view of a nasal speculum 300. As similarly described above, a body 302 of the nasal speculum may taper from a diameter 304 corresponding to an attachment end 306 to a diameter 308 corresponding to an examination end 310 over a length 312. In some embodiments, the diameter 304 may be the same as the diameter 204 of FIG. 6B and/or the diameter 254 of FIG. 7B, as the attachment end 306 may couple to the remote exam attachment 10 and/or the external light attachment 80. On the other hand, the diameter 308 of the examination end 310 may vary from the diameter 208 and/or 258. More specifically, in some embodiments, the examination end 310 may be sized (e.g., at the diameter 308) for positioning within and/or to provide illumination to a patient's nasal passage. Accordingly, in some instances, the diameter 308 may be approximately 11 mm, for example. Further, in some embodiments, the nasal speculum 300 may be sized for positioning at an entrance to the patient's nasal cavity, which may be more readily accessible than a patient's ear canal. Thus, the length 312 may be shorter (e.g., 16 mm) than the length 212, length 262, or both.

It may be appreciated that the speculums, such as 64, 200, 250, and 300, illustrated and described herein may be implemented with any suitable dimensions. That is, for example, while the speculums 64, 200, 250, and 300 may be described as having particular diameters, lengths, and/or relationships between these dimensions, embodiments are not limited thereto.

Figure 9:
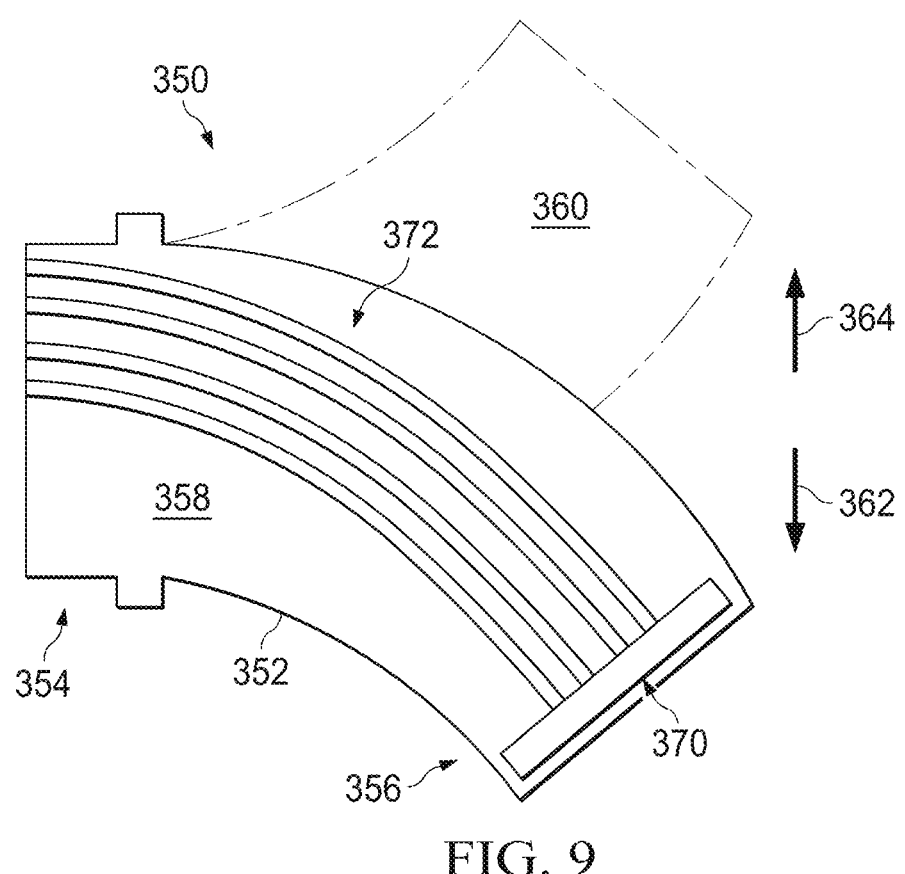
FIG. 9 is a schematic view of a flexible scope, according to embodiments of the present disclosure.

FIG. 9 illustrates a schematic view of a flexible scope 350. In some embodiments, the flexible scope 350 may include a body 352 having an attachment end 354, which may couple to the remote exam attachment 10 and/or the external light attachment 80, as well as an examination end 356. Moreover, the body 352 may bend, or flex, between one or more positions, such as the illustrated first position 358 and second position 360. Accordingly, the body 352 may be formed with a semi-rigid material and/or a set of jointed segments capable of being torqued at one or more joints. Further, while the body 352 is illustrated, as bending in a first direction indicated by arrow 362 or a second direction indicated by arrow 364 between the first position 358 and the second position 360, the body 352 may bend in any suitable direction to any suitable position.

As further illustrated, the flexible scope 350 may include a lens 370 optically coupled to a set of communication relays 372. The set of communication relays 372 may include one or more optical fibers, mirrors, and/or additional lenses. To that end, the lens 370 and the set of communication relays 372 may be positioned within the body 352 and coupled to one another such that light from an object (e.g., an anatomical feature) may be gathered at the examination end 356 and transmitted (e.g., relayed) to the attachment end 354. More specifically, the lens 370 and the set of communication relays 372 may transmit the light from the object such that an image corresponding to the object may be captured at the camera 52. Thus, the lens 370 may focus light from the object at the optical relays, and in some embodiments, the lens 370 may provide magnification.

Additionally, or alternatively, the lens 370 may be included in a camera positioned within the body 352, and the set of communication relays 372 may correspond to a set of communication lines (e.g., electrical communication lines and/or optical fibers). These communication lines may transmit an image captured at the camera within the body 352 to the user device 12. For instance, the communication lines may electrically couple to the cable 86 of the external light attachment 80 and may communicatively couple to the user device 12 via the connector 88 at the electrical port 90. Further, in some embodiments, an image captured at the camera within the body 352 may be transmitted to the user device 12 via a wireless communication interface (e.g., a connection via Bluetooth, Near Field Communication (NFC), Wi-Fi, ZigBee, Li-Fi, cellular data, and/or the like).

Figure 10:
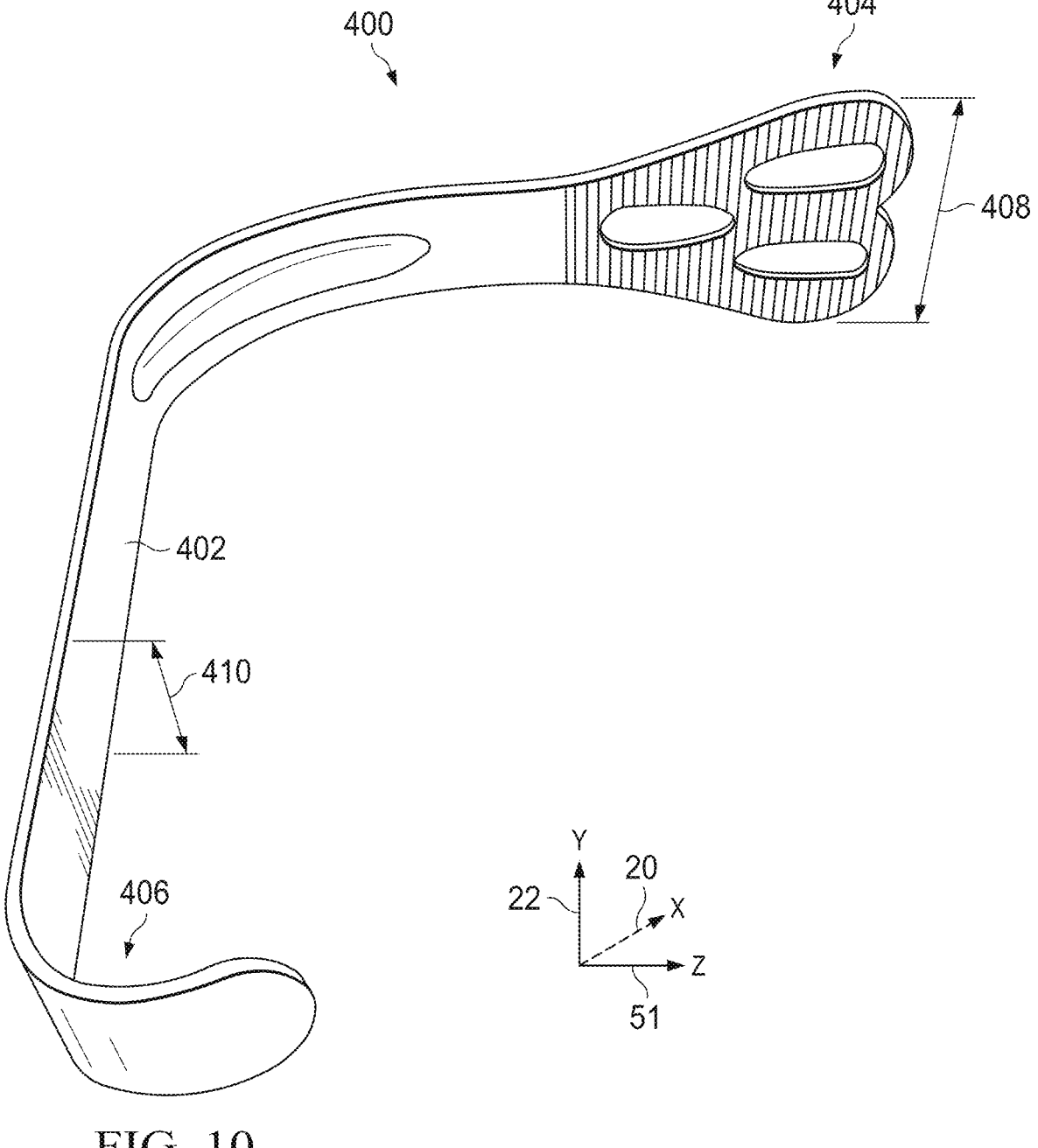
FIG. 10 is a perspective view of a tongue depressor, according to embodiments of the present disclosure.

FIG. 10 illustrates a perspective view of a tongue depressor 400. The tongue depressor 400 includes a handle 402, as well as a depressor end 404. In some embodiments, the handle 402 may be shaped for gripping and/or may include a notched end 406, which prevent the tongue depressor 400 from slipping from a user's hand. The handle 402 may further be shaped to interface with the remote exam attachment 10 and/or the user device 12, as described with reference to FIG. 11. Moreover, the depressor end 404 may be flattened with respect to the y-axis 22 and may be formed with a width 408 greater than a width 410 of the handle 402, as illustrated. Accordingly, the depressor end 404 may be used to immobilize and/or flatten a patient's tongue during examination of a patient's oral cavity and/or throat.

In some embodiments, the tongue depressor 400 may be formed from a stiff material so that the depressor end 404 does not substantially bend or break under pressure exerted at the handle 402 to depress a patient's tongue. For instance, the tongue depressor 400 may be formed with stainless steel, among other suitable materials. Further, in some embodiments, the tongue depressor 400 may be formed from a material, such as stainless steel, that is conducive to reuse. That is, for example, the tongue depressor 400 may be formed from a material that may be washed and/or sterilized between uses, which may enable repeated use of the tongue depressor 400.

Figure 11:
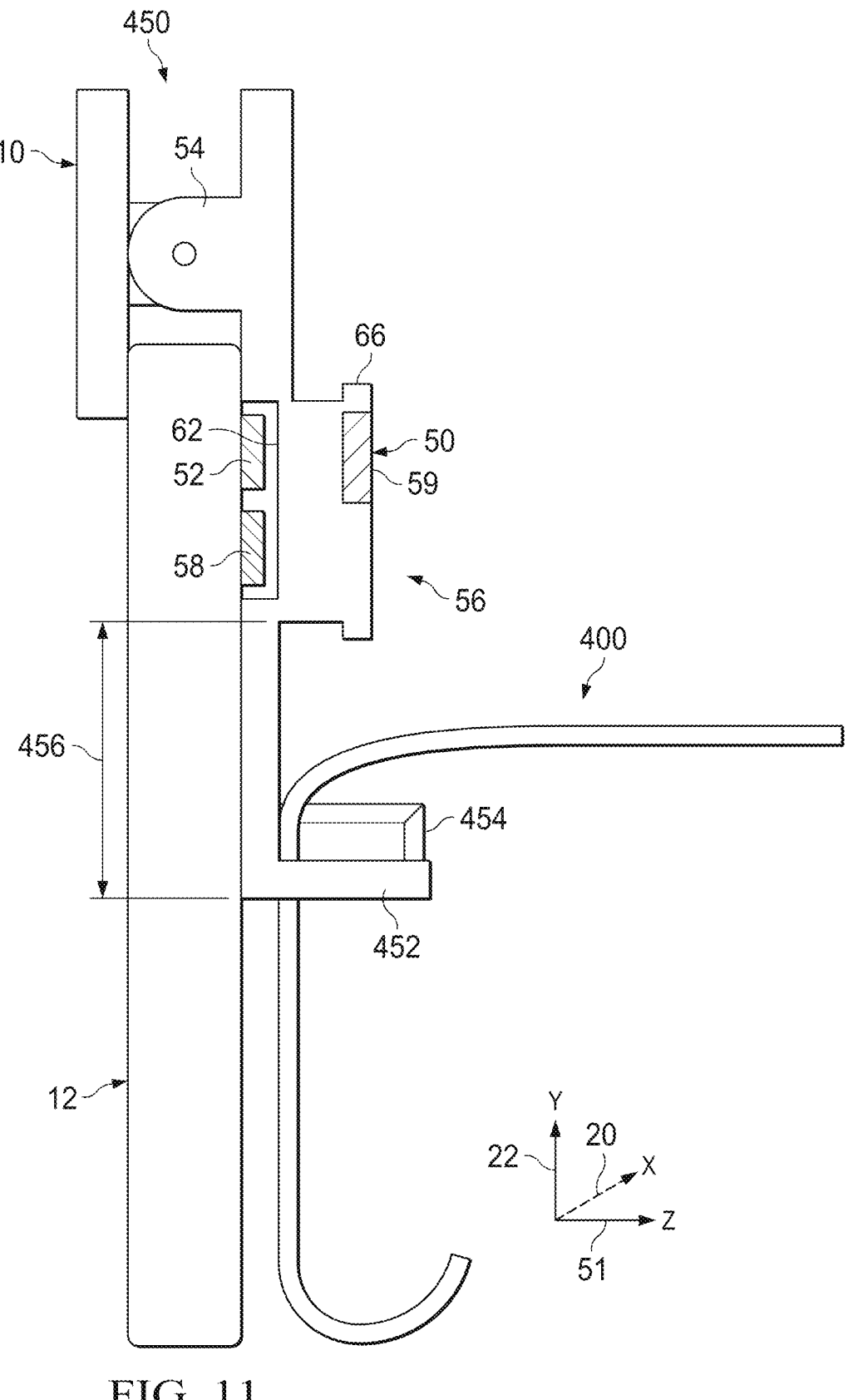
FIG. 11 is a schematic diagram of a side view of a remote exam attachment, a user device, and a tongue depressor, according to embodiments of the present disclosure.

FIG. 11 illustrates a schematic diagram of a side view (corresponding to a plane with respect to the z-axis 51 and the y-axis 22) of remote exam attachment 450 coupled to the tongue depressor 400, as well as the user device 12. The remote exam attachment 450 may be similar to the remote exam attachment 10 described herein. As illustrated, the remote exam attachment 450 may include an arm 452 and may couple to the tongue depressor 400 via the arm 452. In some embodiments, for example, the arm 452 may secure the tongue depressor 400 within a holder and/or with a support 454. For instance, the support 454 may slide, rotate, or otherwise move to allow the tongue depressor 400 to be positioned within the arm 452, and subsequently, the support 454 may be moved to the illustrated position to couple the tongue depressor to the remote exam attachment 450 and/or maintain alignment of the tongue depressor 400 in a certain position. In particular, the arm 452 and/or support 454 may maintain a distance between the imaging assembly 56 and the tongue depressor 400 within a range 456. In this way, even as pressure is exerted at the handle 402, which may pull the depressor end 404 downward (e.g., with respect to the y-axis 22), the distance between the tongue depressor 400 and the imaging assembly 56 may not exceed the range 456. As a result, the imaging assembly 56 may be maintained in a position, with respect to the tongue depressor 400, suitable to capture images for an oral examination. To that end, the user device 12 and the tongue depressor 400 may be moved and used in tandem and/or with one hand, which may improve usability of the remote exam attachment 450 during self-examination.

While the tongue depressor 400 is illustrated as being spaced from the user device 12, it may be appreciated that, when coupled to the remote exam attachment 450, the tongue depressor 400 may be flush with the user device 12. To that end, the tongue depressor 400 may be formed with a flattened handle 402, which may facilitate simultaneous gripping of the handle 402 and the user device 12. Moreover, while the tongue depressor 400 is described as coupling to the remote exam attachment 450 via a support 454, the tongue depressor 400 may additionally or alternatively couple to the remote exam attachment 450 and/or the user device 12 via magnets, a clip-in mechanism, a pressure fit connection, a snap-fit connection, and/or the like. It may further be appreciated that the remote exam attachment 10 may be coupled to both the external light attachment 80 and the tongue depressor 400. In this way, the external light attachment 80 may provide illumination during examination of a patient's oral cavity with the tongue depressor 400, for example.

Figure 12:
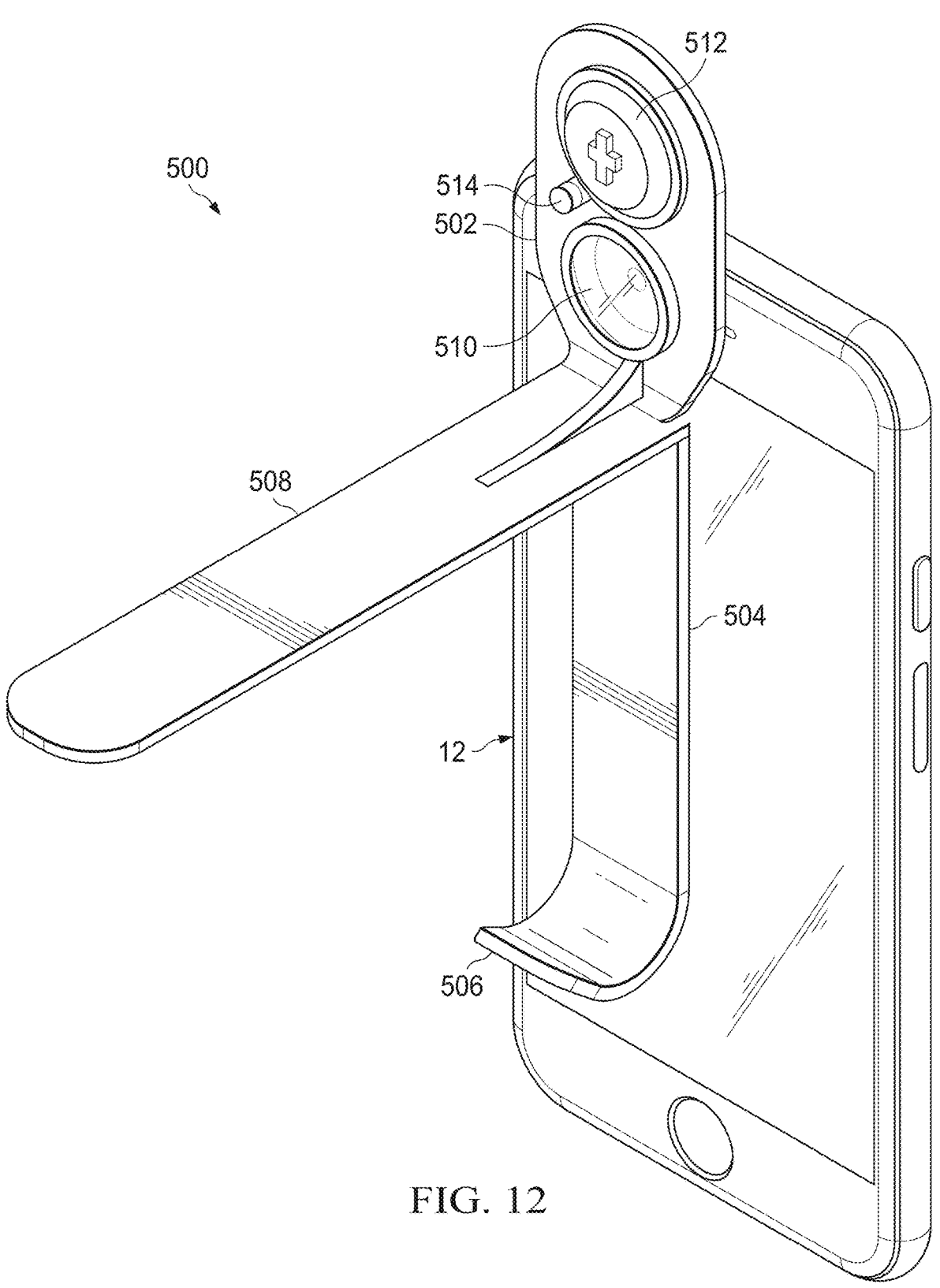
FIG. 12 is a perspective view of a remote exam attachment and a user device, according to embodiments of the present disclosure.

FIG. 12 illustrates a perspective view of an arrangement that includes a remote exam attachment 500 and a user device 12, according to embodiments of the present disclosure. The remote exam attachment 500 may incorporate one or more aspects or features of the remote exam attachments and/or tongue depressors described above with respect to FIGS. 1-4, 10, and 11. As shown in FIG. 12, the remote exam attachment 500 includes a structural body 502. The structural body 502 may be formed of any suitable material, including plastics and/or metals. The structural body 502 includes an elongated portion 504. The elongated portion 504 may be sized and shaped to interface with the back of the user device 12. In some instances, the elongated portion 504 is sized and shaped to sit flush against a back surface of the user device 12. The structural body 502 also includes a distal portion 506. In the illustrated example, the distal portion 506 curves outward from the elongated portion 504 such that the distal portion 506 extends away from the user device 12. In other instances, the distal portion 506 may extend at an oblique or perpendicular angle relative to the elongated portion 504. The distal portion 506 may serve as a tactile reference and/or grip structure for a user. In this regard, a user may utilize the distal portion 506 to maintain the position of the remote exam attachment 500 relative to the user device 12 in some instances.

The structural body 502 of the remote exam attachment 500 also includes a tongue depressor 508. The tongue depressor 508 may be rigidly attached to the elongated portion 504. In other instances, the tongue depressor 508 may be pivotally attached to the elongated portion 504 such that the tongue depressor can transition from an expanded position (as shown in FIG. 12) to a retracted or reduced profile position. In some instances, the tongue depressor 508 may extend downward toward or to the distal portion 506 in the retracted or reduced profile position.

The remote exam attachment 500 also includes a lens 510 coupled to the structural body 502. The lens 510 may be similar to the lens 50 described above with reference to FIGS. 3 and 4. In this regard, the lens 510 may be configured to be aligned with a front-facing camera lens of the user device 12. The lens 510 may be configured to provide magnification (e.g., 1.5×, 2×, 3×, 5×, 6× magnification, and/or the like) to an image captured by the front-facing camera. In some instances, the remote exam attachment 500 and/or the structural body 502 may be configured such that the different lenses 510 having different optical characteristics may be interchangeably coupled to the structural body 502. Further, in some instances, the remote exam attachment 500 and/or the structural body 502 may be configured to facilitate the use of multiple lenses simultaneously.

The remote exam attachment 500 also includes a light source 512 and optical element 514. In this regard, the light source 512 and optical element 514 may be utilized to generate sufficient illumination to inner cavities (e.g., throat, ear, nose, etc.) of the patient to obtain suitable photos and/or videos. The light source 512 may be any suitable light source, including a fiber optic light source, a laser light source, a light emitting diode (LED), or otherwise. The light source 512 may include a dedicated and/or integrated power supply. Alternatively, the light source 512 may draw power from the user device 12. The optical element 514 may be an optical fiber, a light pipe, an LED, or other suitable component to output light/energy generated by the light source 512.

Figure 13:
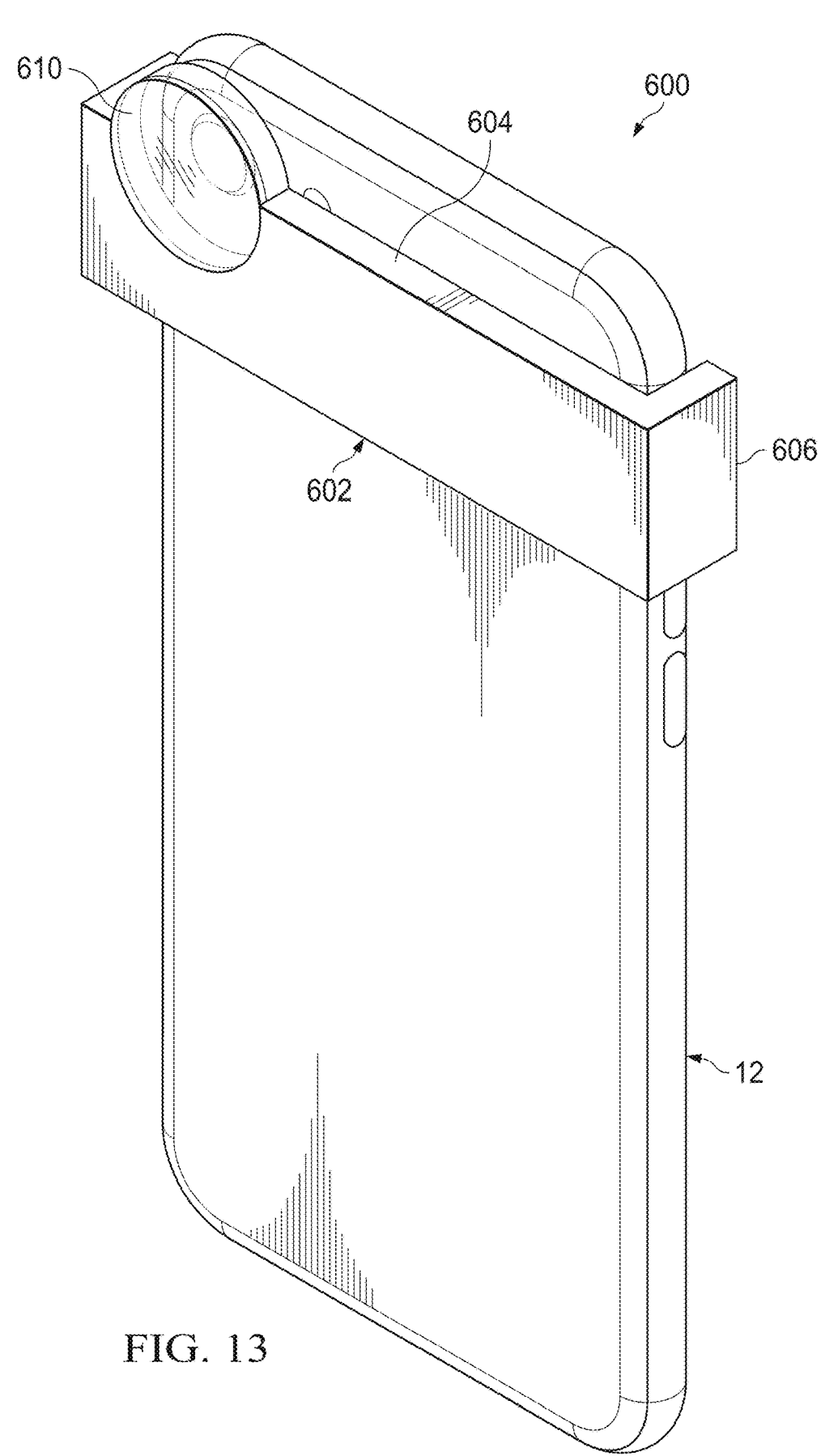
FIG. 13 is a perspective view of a remote exam attachment and a user device, according to embodiments of the present disclosure.

FIG. 13 is a perspective view of a remote exam attachment 600 and a user device 12, according to embodiments of the present disclosure. The remote exam attachment 600 may incorporate one or more aspects or features of the remote exam attachments described above with respect to FIGS. 1-4 and 10-12. As shown in FIG. 13, the remote exam attachment 600 includes a structural body 602. The structural body 602 may be formed of any suitable material, including plastics and/or metals. The structural body 602 includes an elongated portion 604. The elongated portion 604 may be sized and shaped to interface with the back of the user device 12. In some instances, the elongated portion 604 is sized and shaped to sit flush against a back surface of the user device 12 and extend to each side of the user device 12. The structural body 602 also includes a lateral arm 606 on each end of the elongated portion 604. The lateral arms 606 may be spring-loaded relative to elongated portion 604. In the illustrated example, the lateral arms 606 extend perpendicular to the elongated portion 604 such that the lateral arms 606, along with the elongated portion 604, securely engage the user device 12. In some instances, a portion of the lateral arms 606 extend partially across a front surface of the user device. The spring-loaded nature of the lateral arms 606 allows the user device 12 to be inserted into the structural body 602 and securely held in place. Further, the spring-loaded nature can allow for use of the same structural body 602 with multiple different types and/or sizes of phones. Other mounting structures based on spring-loaded and/or resiliently deformable plastics or other materials may be used in a similar manner to couple the remote exam attachment 600 to the user device.

The remote exam attachment 600 also includes a lens 610 coupled to the structural body 602. The lens 610 may include some features similar to the lenses 50 and 510 described above with reference to FIGS. 3, 4, and 12. In this regard, the lens 610 may be configured to be aligned with a front-facing camera lens of the user device 12. The lens 610 may be configured to provide magnification (e.g., 1.5×, 2×, 3×, 5×, 6× magnification, and/or the like) to an image captured by the front-facing camera. In some instances, the remote exam attachment 600 and/or the structural body 602 may be configured such that the different lenses 610 having different optical characteristics may be interchangeably coupled to the structural body 602. Further, in some instances, the remote exam attachment 600 and/or the structural body 602 may be configured to facilitate the use of multiple lenses simultaneously.

Figure 14:
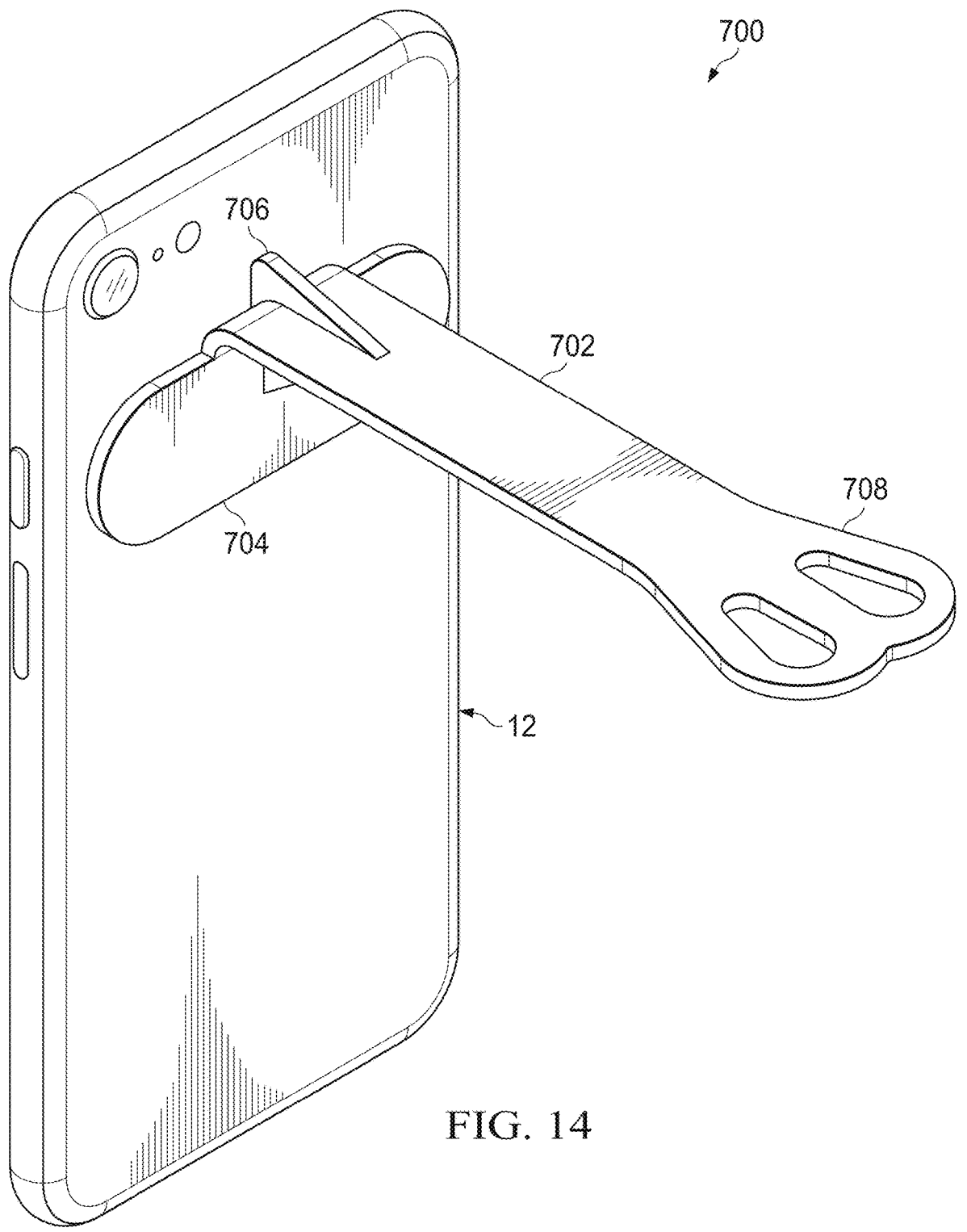
FIG. 14 is a perspective view of a remote exam attachment and a user device, according to embodiments of the present disclosure.

FIG. 14 is a perspective view of a user device 12 and a remote exam attachment 700, according to embodiments of the present disclosure. The remote exam attachment 700 may incorporate one or more aspects or features of the remote exam attachments and/or tongue depressors described above with respect to FIGS. 1-4 and 10-13. As shown in FIG. 14, the remote exam attachment 700 includes a structural body 702. The structural body 702 may be formed of any suitable material, including plastics and/or metals. The structural body 702 includes an interface portion 704. The interface portion 704 may be sized and shaped to interface with the back of the user device 12. In some instances, the interface portion 704 is sized and shaped to sit flush against a back surface of the user device 12. In some aspects, the interface portion 704 may be sized and shaped to allow a user to hold the remote exam attachment 700 against the user device 12 using the interface portion 704. In this regard, the remote exam attachment 700 may not fixedly secure to the user device 12 via clip, clamp, or other mechanism. Instead, the remote exam attachment 700 may be held in place relative to the user device by a user. For example, a user may apply one or both thumbs to the interface portion 704, while using other fingers to grasp the sides and/or front of the user device 12. In this way, a user can easily position and reposition the remote exam attachment 700 relative to the user device 12 and, in particular, relative to one or more cameras and/or light sources of the user device 12 in order to obtain pictures and/or videos of the patient's anatomy. In some instances, the user is the patient (see, e.g., FIG. 15).

The structural body 702 may also include a structural fin 706. In the illustrated example, the structural fin 706 extends in a direction opposite of the interface portion 704 relative to a tongue depressor 708 of the remote exam attachment 700. In this regard, the structural fin 706 may provide structural integrity to the structural body 702 to counter the loads that may result from a user applying pressure on a distal end of the tongue depressor 708. Further, the structural fin 706 may help maintain the position of the remote exam attachment 700 relative to the user device 12 under such loading conditions.

The structural body 702 of the remote exam attachment 700 also includes a tongue depressor 708. The tongue depressor 708 may be rigidly attached to the interface portion 704 and/or the structural fin 706. In other instances, the tongue depressor 708 may be pivotally attached to the interface portion 704 and/or the structural fin 706 such that the tongue depressor can transition from an expanded position (as shown in FIG. 14) to a retracted or reduced profile position. In some instances, the tongue depressor 708 may extend downward (e.g., along the backside of the user device 12) in the retracted or reduced profile position.

Figure 15:
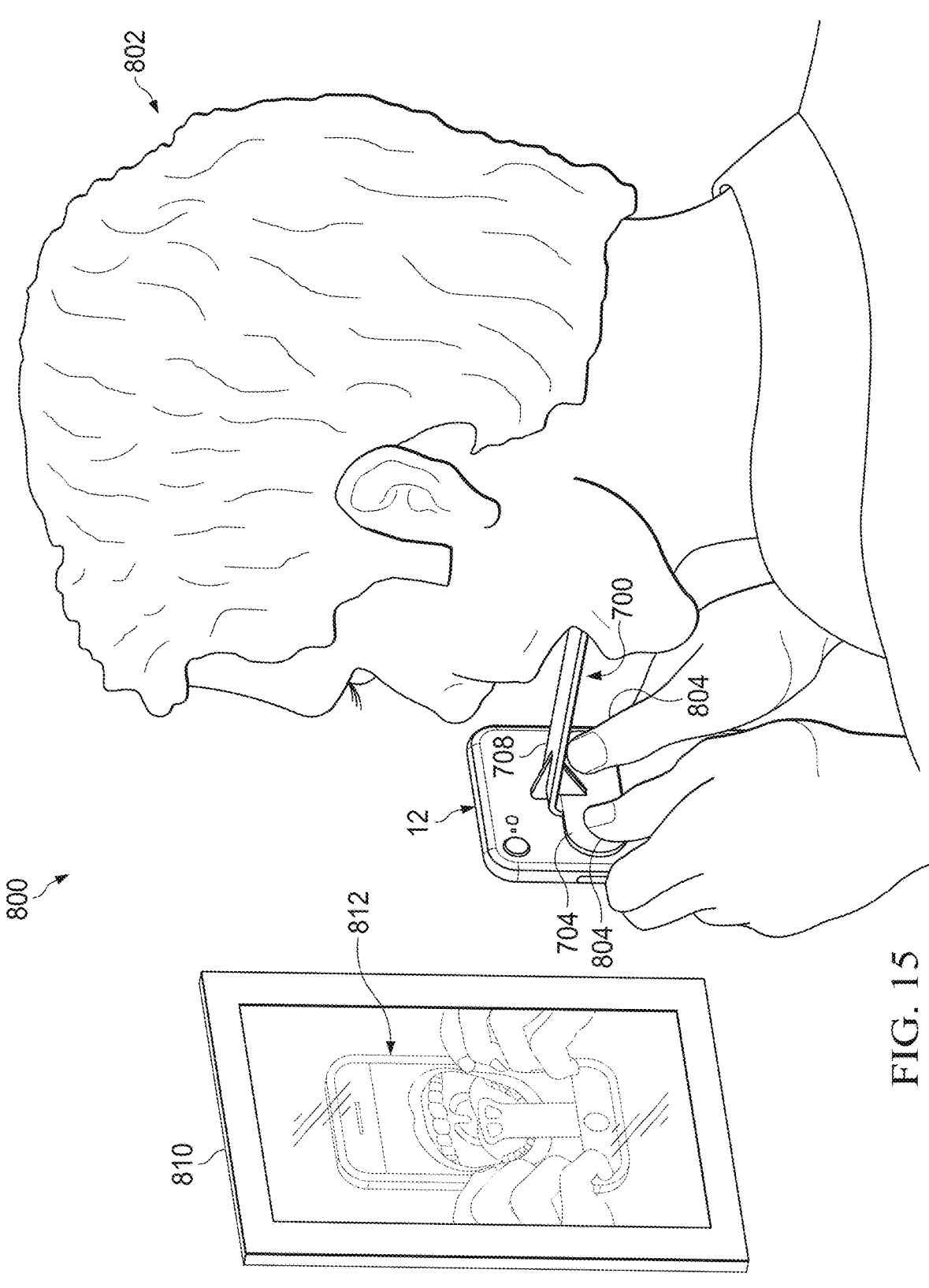
FIG. 15 is a perspective view of a user using the remote exam attachment of FIG. 14 with a mirror, according to embodiments of the present disclosure.

FIG. 15 is a perspective view of an arrangement 800 showing a user 802 using the remote exam attachment 700 of FIG. 14 with a mirror 810, according to embodiments of the present disclosure. As shown, the user 802 can position the remote exam attachment 700 such that the interface portion 704 is held against the back of the user device 12 while a distal end of the tongue depressor 708 extends within a mouth of the user 802. The user 802 may use one or both thumbs 804 to hold the interface portion 704 against the user device 12. Further, the user 802 may adjust the relative position of the remote exam attachment 700 such that a front-facing camera of the user device 12 is able to capture to a suitable image/video of the relevant anatomy inside the user's mouth. In this regard, the user 802 may utilize a mirror 810 to view the display of the user device 12 to determine what positional adjustments (e.g., of the remote exam attachment 700, the user device 12, and/or the user 802), if any, may be needed to obtain the desired image/video. For example, as shown the user 802 may see a reflection of the user interface 812 of the user device 12 in the mirror showing a preview of the image/video and/or the current view of the camera and can adjust positioning as needed. Once the user 802 sees a satisfactory preview of the image/video and/or the current view of the camera, then the user 802 can actuate the camera of the user device to obtain the image/video. The approach shown in FIG. 15 can be adapted to be used with other remote exam attachments of the present disclosure.

In some instances, instead of the user 802 using the remote exam attachment 700 and user device 12 to obtain image(s)/video(s) of the user's anatomy, the user 802 can utilize the remote exam attachment 700 (or any other remote exam attachment and/or associated components of the present disclosure) to obtain image(s)/video(s) of another person's anatomy. This may be particularly useful for patients that are children, elderly, and/or otherwise may have difficultly self-administering the remote exam attachment 700 and user device 12. In such instances, the user 802 may directly view the user interface of the user device 12 (e.g., without use of a mirror) to see a preview of the image/video and/or the current view of the camera and can adjust positioning of the remote exam attachment 700, the user device 12, and/or the patient, as needed.

In some instances, a method of remote medical examination comprises coupling a remote exam attachment to a user device; positioning, with the remote exam attachment coupled to the user device, a portion of the remote exam attachment in proximity to an orifice of a patient such that a camera of the user device is oriented to capture an image of a region of interest within the orifice; and obtaining, with the portion of the remote exam attachment in proximity to the orifice of the patient, one or more images of the region of interest with the camera of the user device. The camera of the user device may be a front-facing camera. Also, the positioning of the portion of the remote exam attachment in proximity to the orifice of the patient and the obtaining the one or more images of the region of interest with the camera of the user device may be performed by the patient or another user. In some instances, the method includes determining, by the patient, that the camera of the user device is oriented to capture the image of the region of interest within the orifice based on display of the user device. In this regard, the determining that the camera of the user device is oriented to capture the image of the region of interest within the orifice based on display of the user device may include viewing a reflection of the display in a reflective surface, such as a mirror. In some instances, the portion of the remote exam attachment positioned in proximity to the orifice of the patient comprises at least part of a tongue depressor. The orifice of the patient may be a mouth of the patient. In some instances, the portion of the remote exam attachment positioned in proximity to the orifice of the patient comprises at least part of a speculum. The orifice of the patient may be at least one of an ear or a nose of the patient.

Figure 16:
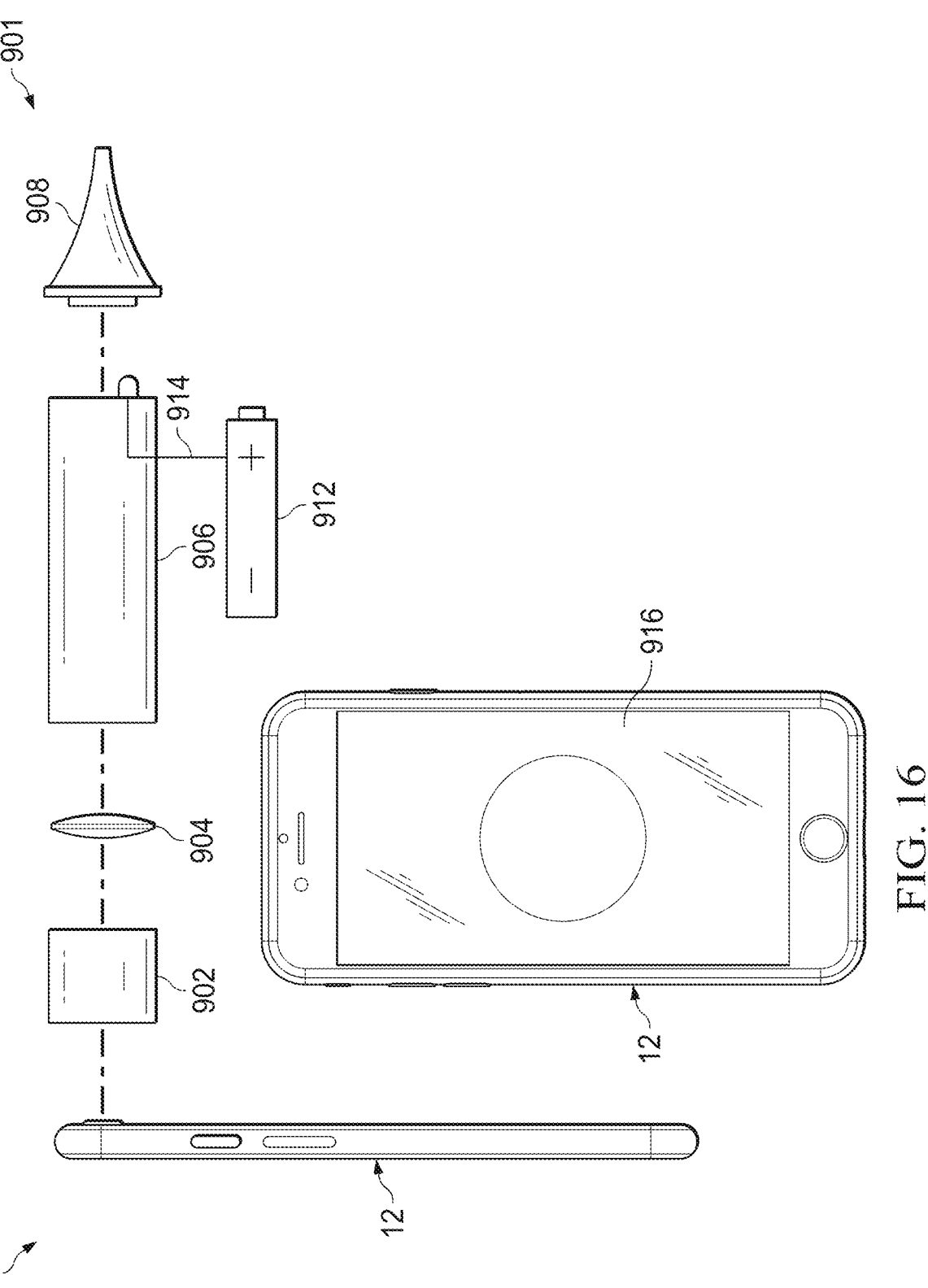
FIG. 16 is a schematic diagram of a side, exploded view of a remote exam system, according to embodiments of the present disclosure.

FIG. 16 is a schematic diagram of a side, exploded view of a remote exam system 900, according to embodiments of the present disclosure. The remote exam system 900 may incorporate one or more aspects or features of the remote exam attachments and/or speculums described above with respect to FIGS. 1-15. As shown in FIG. 16, the remote exam system 900 includes a user device 12 and a remote exam attachment 901. The remote exam attachment 901 can include a spacer 902, one or more optical elements 904, a housing 906, a speculum 908, a light source 912, and a light path 914. Further, the user device 12 may include and/or execute an application 916 that is used in conjunction with the remote exam attachment 901 to obtain image(s)/video(s) of patient anatomy. In particular, the application 916 may control one or more aspects of the user device 12 and/or the remote exam attachment 901, including without limitation camera settings (e.g., angular field of view, focus depth, digital zoom parameters, image processing parameters (e.g., noise, low-light processing, etc.), etc.) and/or light settings (e.g., light source on/off, timing of light source on/off, brightness of emitted light, and/or other lighting parameters of the light source 910 and/or a light source/flash of the user device 12). In some instances, the application 916 is configured to crop a raw image obtained by the camera of the user device 12 to mimic the field of view through a speculum with the natural eye.

The spacer 902 may be formed of any suitable material, including plastics and/or metals. A proximal portion of the spacer 902 may be sized and shaped to interface with one or more camera lenses on the back of the user device 12. In some instances, the proximal portion of the spacer 902 is sized and shaped to engage a back surface of the user device 12 such that an optical path of the remote exam attachment 901 can be aligned with an optical path of one or more forward-facing cameras of the user device 12. While illustrated as being cylindrical, the proximal portion of the spacer may have other shapes (e.g., rectangular, square, rounded rectangular, rounded square, geometrical, custom based on user device structural features, etc.). The spacer 902 may transition from a non-cylindrical shape to a cylindrical shape along its length in some instances.

A distal portion of the spacer 902 may be sized and shaped to interface with the optical element 904 and/or the housing 906. Each of the one or more optical elements 904 may be a lens (e.g., similar to the lenses 50, 510) described above with reference to FIGS. 3, 4, and/or 12. In some instances, two or more of the spacer 902, one or more optical elements 904, and the housing 906 are integrated into a single component. In other instances, two or more of the spacer 902, one or more optical elements 904, and the housing 906 are separate components that are coupled together (e.g., via threaded engagement, snap-fit, or other engagement structures) for use as the remote exam attachment 901. In some instances, the one or more optical elements 904 are fixedly secured within the housing 906. In this regard, in some instances multiple housings 906 having different optical element(s) may be supplied with the remote exam attachment 901. The different optical element(s) may be configured to facilitate viewing of particular anatomical features, at particular focal depths, at particular fields of view, and/or combinations thereof. Accordingly, a user may select the housing 906 with the appropriate optical element(s) for the intended use.

The speculum 908 of the remote exam attachment 901 may be removably coupled to the distal portion of the housing 906. In other instances, the speculum 908 may be fixedly attached to the housing 906. In some instances, multiple speculums 908 having different sizes and/or optical properties may be supplied with the remote exam attachment 901. The different speculum may be configured to facilitate viewing of particular anatomical features, within particular anatomical orifices, at particular focal depths, at particular fields of view, and/or combinations thereof. Accordingly, a user may select the speculum 908 sized and shaped and/or with the optical features for the intended use.

The remote exam attachment 901 also includes the light source 912 and the light path 914. In this regard, the light source 912 and the light path 914 may be utilized to generate sufficient illumination to inner cavities (e.g., throat, ear, nose, etc.) of the patient to obtain suitable photos and/or videos. The light source 912 may be any suitable light source, including a fiber optic light source, a laser light source, a light emitting diode (LED), or otherwise. The light source 912 may include a dedicated and/or integrated power supply (e.g., battery, capacitor, etc.). Alternatively, the light source 912 may draw power from the user device 12. The light path 914 may include an optical fiber, a light pipe, an LED, or other suitable component(s) to output light/energy generated by the light source 912. In some instances, the light path 914 may extend at least partially within the speculum 908. In some instances, the light path 914 may be positioned adjacent to, but outside of the speculum 908. In some aspects, the light path 914 is coupled to a light source of the user device 12 instead of the light source 912. That is, the light source 912 may be omitted and the light path 914 may interface with a light source (e.g., external flash or flash light) of the user device 12.

Figure 17:
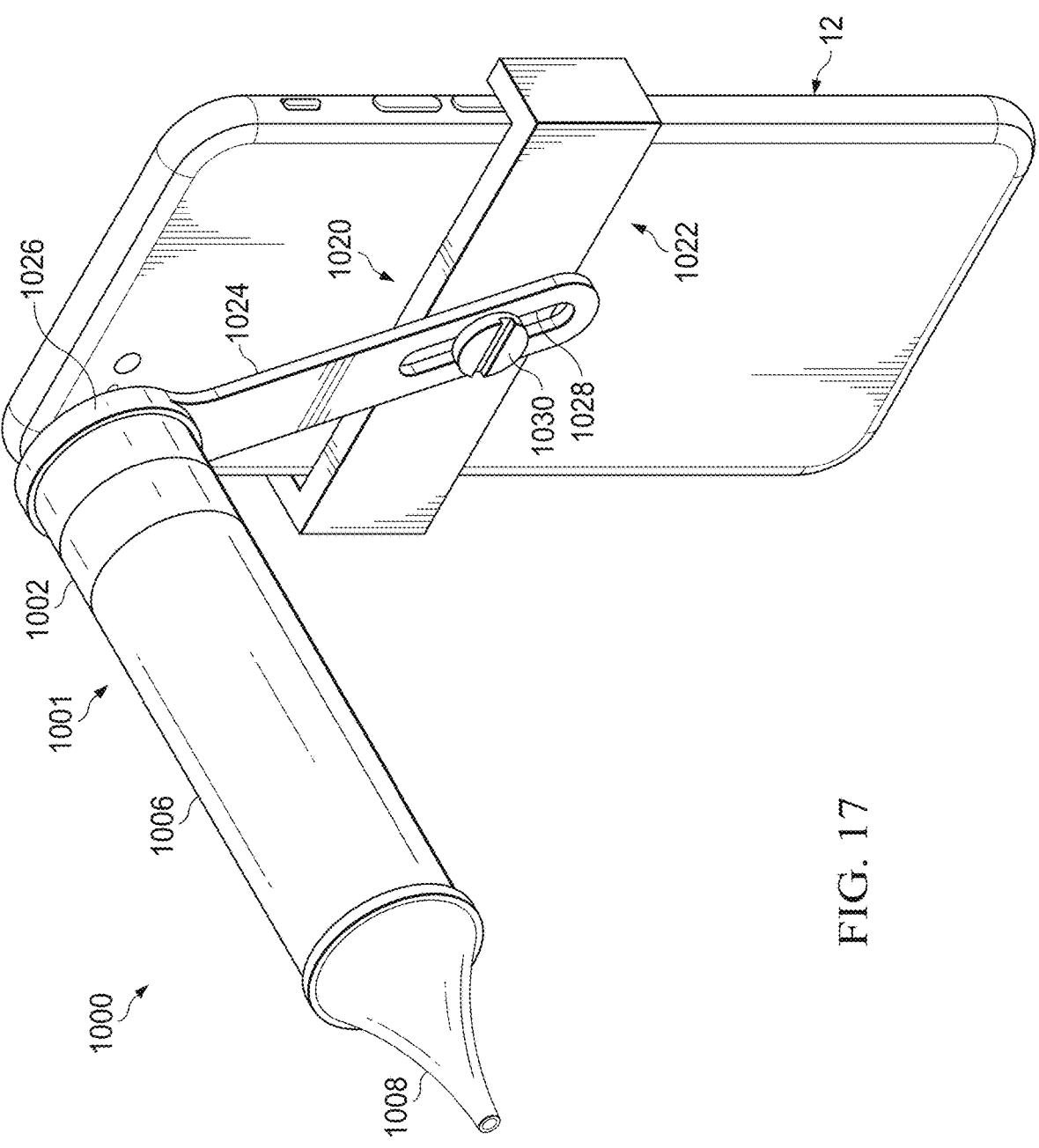
FIG. 17 is a perspective view of a remote exam system, according to embodiments of the present disclosure.
Figure 18:
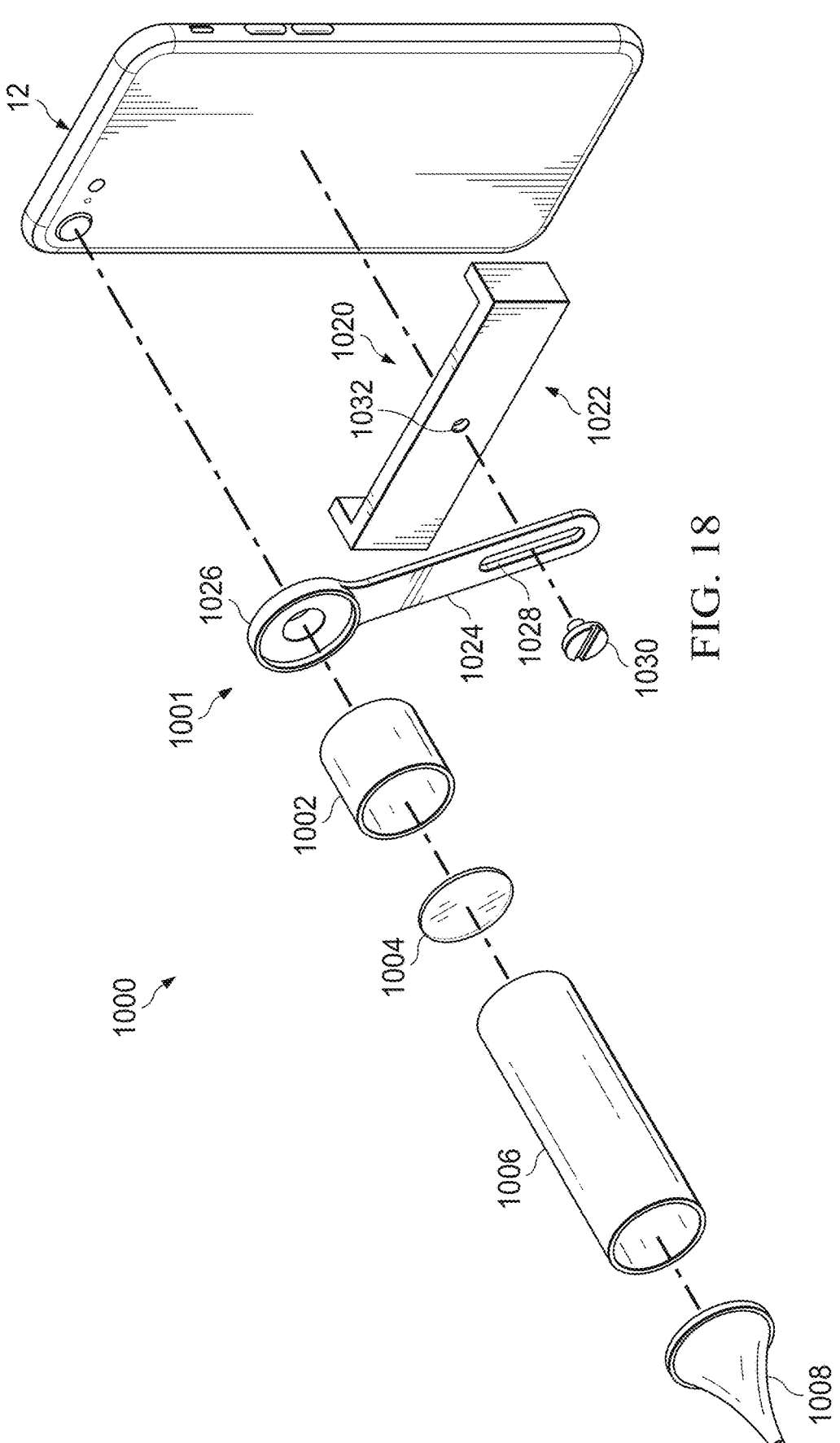
FIG. 18 is an exploded perspective view of the remote exam system of FIG. 17, according to embodiments of the present disclosure.

Referring now to FIGS. 17 and 18, shown therein is a remote exam system 1000, according to embodiments of the present disclosure. FIG. 17 is a perspective view of the remote exam system 1000, according to embodiments of the present disclosure. FIG. 18 is an exploded perspective view of the remote exam system 1000 of FIG. 17, according to embodiments of the present disclosure. The remote exam system 1000 may incorporate one or more aspects or features of the remote exam attachments and/or speculums described above with respect to FIGS. 1-16. The illustrated example of FIGS. 17 and 18 includes many features similar to the remote exam system 900 of FIG. 16. Accordingly, details regarding each element of the remote exam system 1000 will not be repeated here. The remote exam system 1000 includes a user device 12 and a remote exam attachment 1001. The remote exam attachment 1001 can include a spacer 1002, a housing 1006, a speculum 1008, and a mounting structure 1020. The remote exam attachment 1001 may include one or more optical elements or lenses within the spacer 1002, the housing 1006, and/or the speculum 1008. In some instances, the remote exam attachment 1001 further includes a light source and/or a light path.

The mounting structure 1020 may be utilized to removably couple the spacer 1002, the housing 1006, and/or the speculum 1008 to the user device 12. In particular, the mounting structure 1020 may be utilized to removably couple the spacer 1002, the housing 1006, and/or the speculum 1008 to the user device 12 such that an optical path of the remote exam system is aligned with a camera (e.g., front-facing or rear-facing) of the user device 12. The components of the mounting structure may be formed of any suitable material, including plastics and/or metals. As shown, the mounting structure 1020 includes a mounting clamp 1022. The mounting clamp 1022 may be similar to structural body 602 described above with respect to FIG. 13.

The mounting structure 1020 may further include an elongated portion 1024 extending from the mounting clamp 1022. The elongated portion 1024 may have a distal portion 1026 sized and shaped to interface with the spacer 1002. In some instances, the distal portion 1026 is sized and shaped to receive and/or couple with a proximal portion of the spacer 1002. In some instances, the distal portion 1026 of the elongated portion 1024 of the mounting structure is permanently and/or fixedly secured to the spacer 1002 and/or the housing 1006. As shown, a proximal portion of the elongated portion 1024 includes a slot 1028. The slot 1028 extends linearly along the length of the elongated portion 1024. A screw 1030 (or other selectively locking mechanism) couples the elongated portion 1024 to the mounting clamp 1022. In particular, as shown in FIG. 18, the screw 1030 extends through the slot 1028 and threadingly engages an opening 1032 in the mounting clamp 1022. The interface of the slot 1028 with the screw 1030 allows the elongated portion 1024 to move linearly along the length of the slot 1028 and pivot about the screw 1030 when the screw is loosened. This movement allows a user to adjust the alignment of an optical axis of the remote exam attachment 1001 with a camera of the user device 12. Once the remote exam attachment 1001 is properly aligned relative to the user device 12, the screw 1030 can be tightened to secure the relative position of the remote exam attachment 1001. It will be appreciated that different and/multiple locking mechanisms may be used to hold the position of the remote exam attachment 1001 relative to the user device 12 once the desired alignment is achieved.

Figure 19:
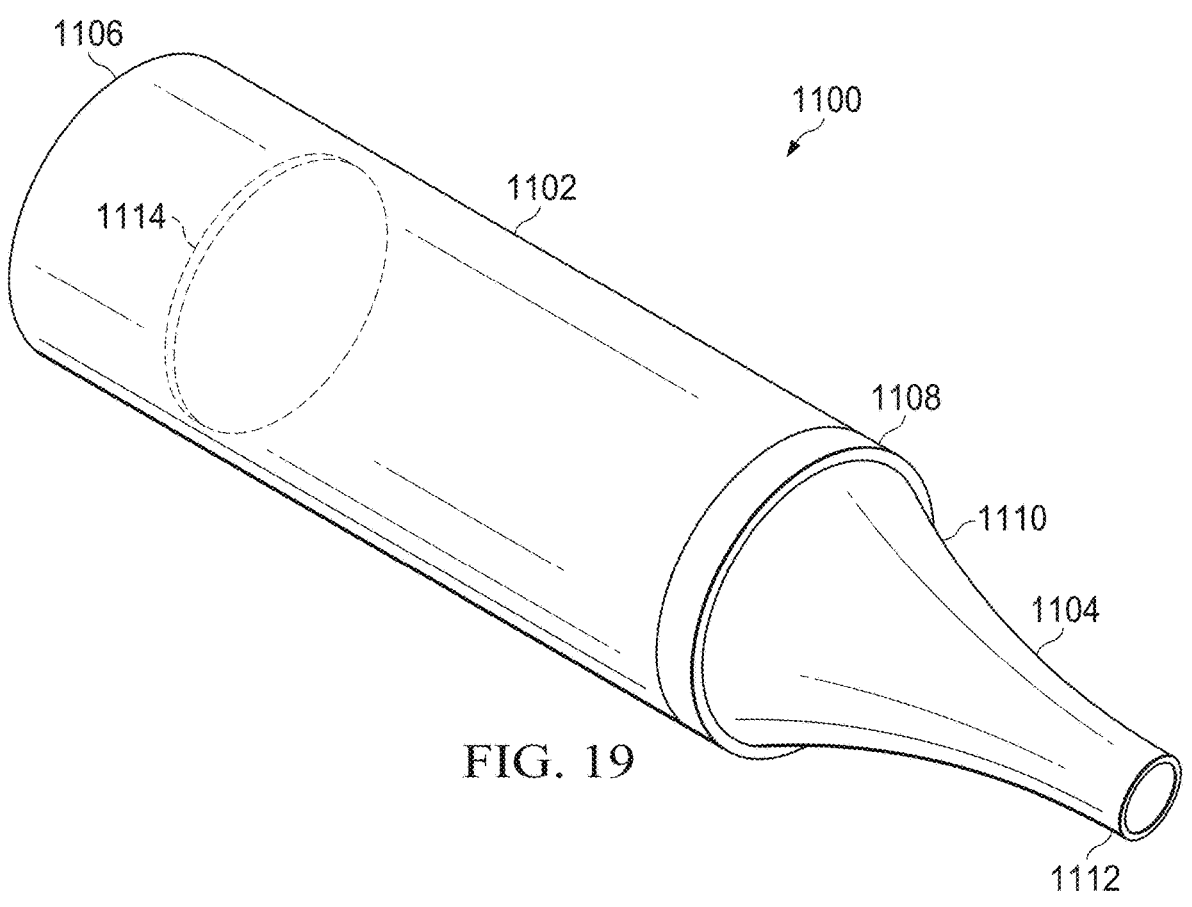
FIG. 19 is a perspective view of a speculum, according to embodiments of the present disclosure.

FIG. 19 is a perspective view of a speculum 1100, according to embodiments of the present disclosure. The speculum 1100 includes a main body 1102 and a patient interface 1104. The main body 1102 includes a proximal portion 1106 and a distal portion 1108. Similarly, the patient interface 1104 includes a proximal portion 1110 and a distal portion 1112. In some instances, the distal portion 1108 of the main body 1102 is configured to interface with the proximal portion 1110 of the patient interface 1104. For example, the distal portion 1108 of the main body 1102 may receive the proximal portion 1110 of the patient interface 1104 via an interference/press fit, snap fit, a threaded engagement, and/or other engagement type such that the patient interface 1104 is, at least temporarily, held in a fixed position relative to the main body 1102. In other instances, the main body 1102 and the patient interface 1104 are integrally formed. In the illustrated embodiment, the main body 1102 also includes an optical element 1114. The optical elements 1114 may be a lens. In some instances, the length of the main body 1102 provides sufficient linear distances to allow the use of a single optical element. In this regard, the length of the main body 1102 may be between about 3 cm and about 10 cm, or other suitable length. In other instances, the main body 1102 includes two or more optical elements. The optical element(s) within the main body 1102 may be selected to achieve a desired focus depth, field of view, and/or other imaging/video parameters.

Figure 20:
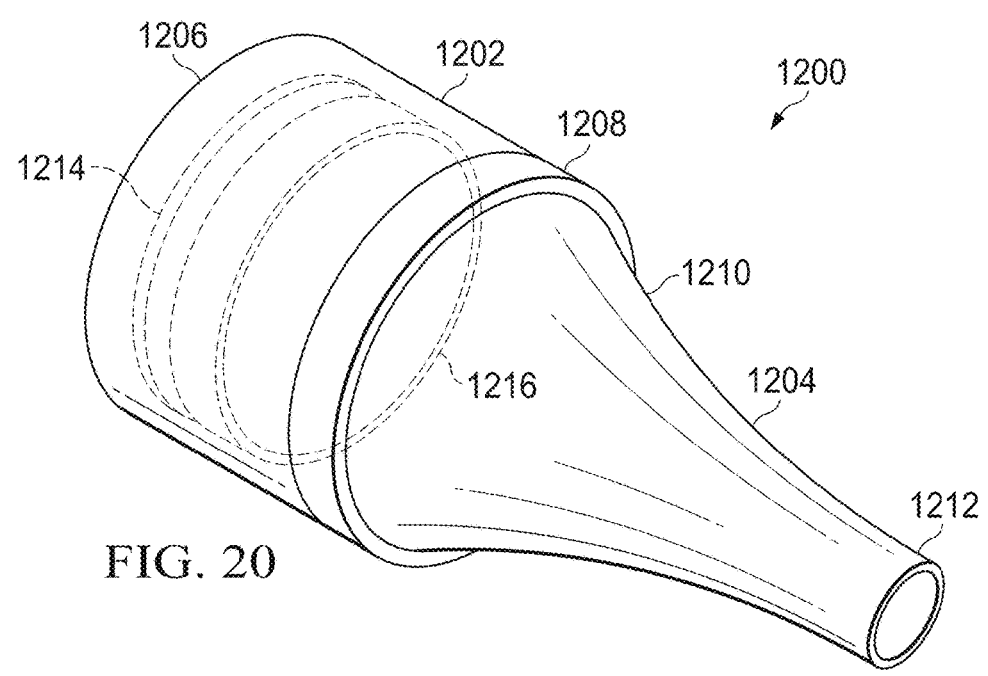
FIG. 20 is a perspective view of a speculum, according to embodiments of the present disclosure.

FIG. 20 is a perspective view of a speculum 1200, according to embodiments of the present disclosure. The speculum 1200 includes a main body 1202 and a patient interface 1204. The main body 1202 includes a proximal portion 1206 and a distal portion 1208. Similarly, the patient interface 1204 includes a proximal portion 1210 and a distal portion 1212. In some instances, the distal portion 1208 of the main body 1202 is configured to interface with the proximal portion 1210 of the patient interface 1204. For example, the distal portion 1208 of the main body 1202 may receive the proximal portion 1210 of the patient interface 1104 via an interference/press fit, snap fit, a threaded engagement, and/or other engagement type such that the patient interface 1204 is, at least temporarily, held in a fixed position relative to the main body 1202. In other instances, the main body 1202 and the patient interface 1204 are integrally formed. In the illustrated embodiment, the main body 1202 also includes an optical element 1214 and an optical element 1216. The optical elements 1214 and 1216 may be lenses. In some instances, the length of the main body 1202 is reduced (e.g., relative to the main body 1102 of the speculum 1100) to provide a smaller form factor that can be more user friendly in some situations. However, the reduced length may require the use of multiple optical elements to achieve a desired focal length and/or field of view. In this regard, in some instances the length of the main body 1202 may be between about 1 cm and about 4 cm, or other suitable length. In other instances, the main body 1102 includes a single optical element. In yet other instances, the main body 1102 includes three or more optical elements. The one or more optical elements within the main body 1102 may be selected to achieve a desired focus depth, field of view, and/or other imaging/video parameters.

Figure 22:
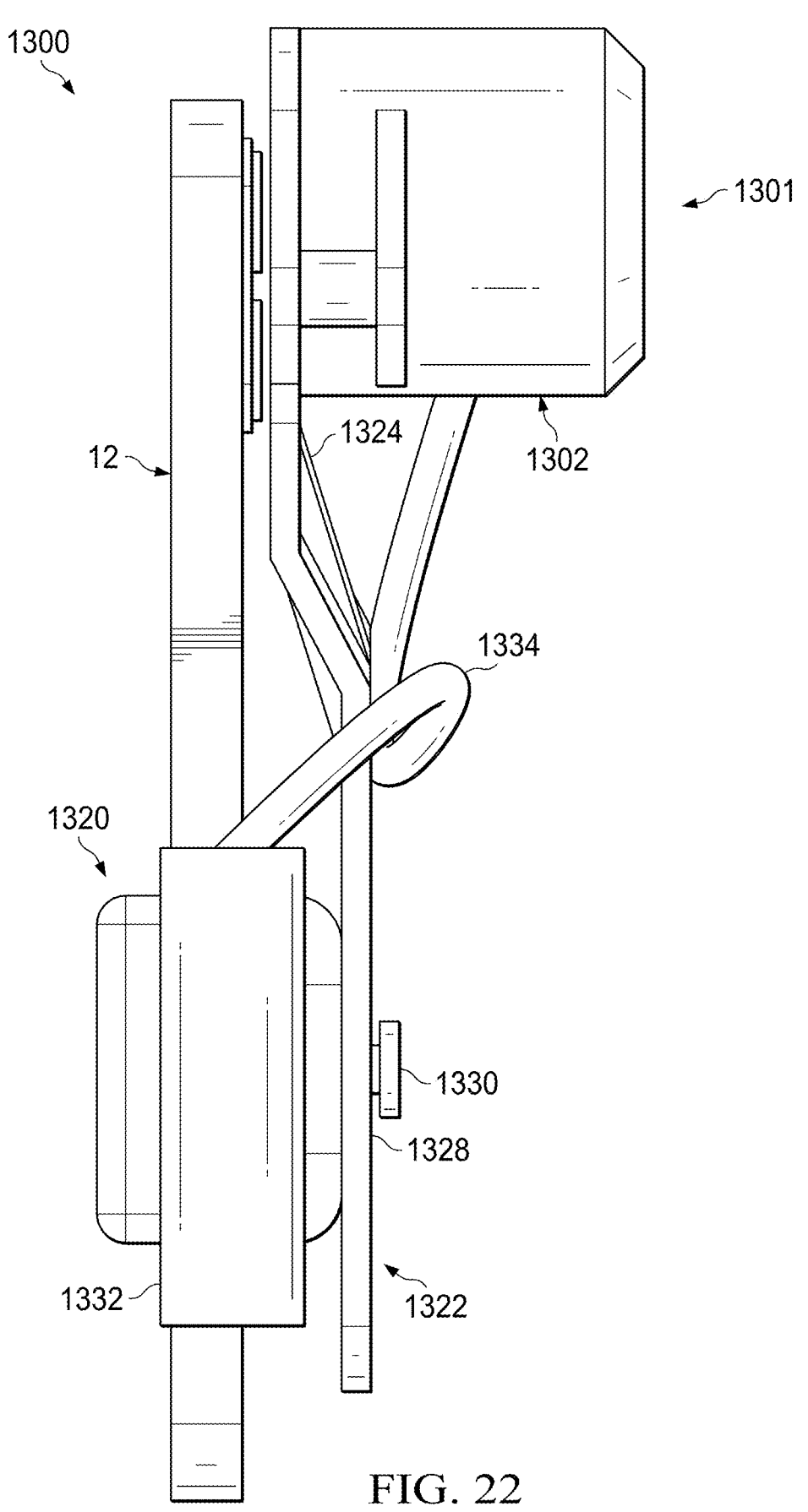
FIG. 22 is side view of the remote exam system of FIG. 21, according to embodiments of the present disclosure.
Figure 23:
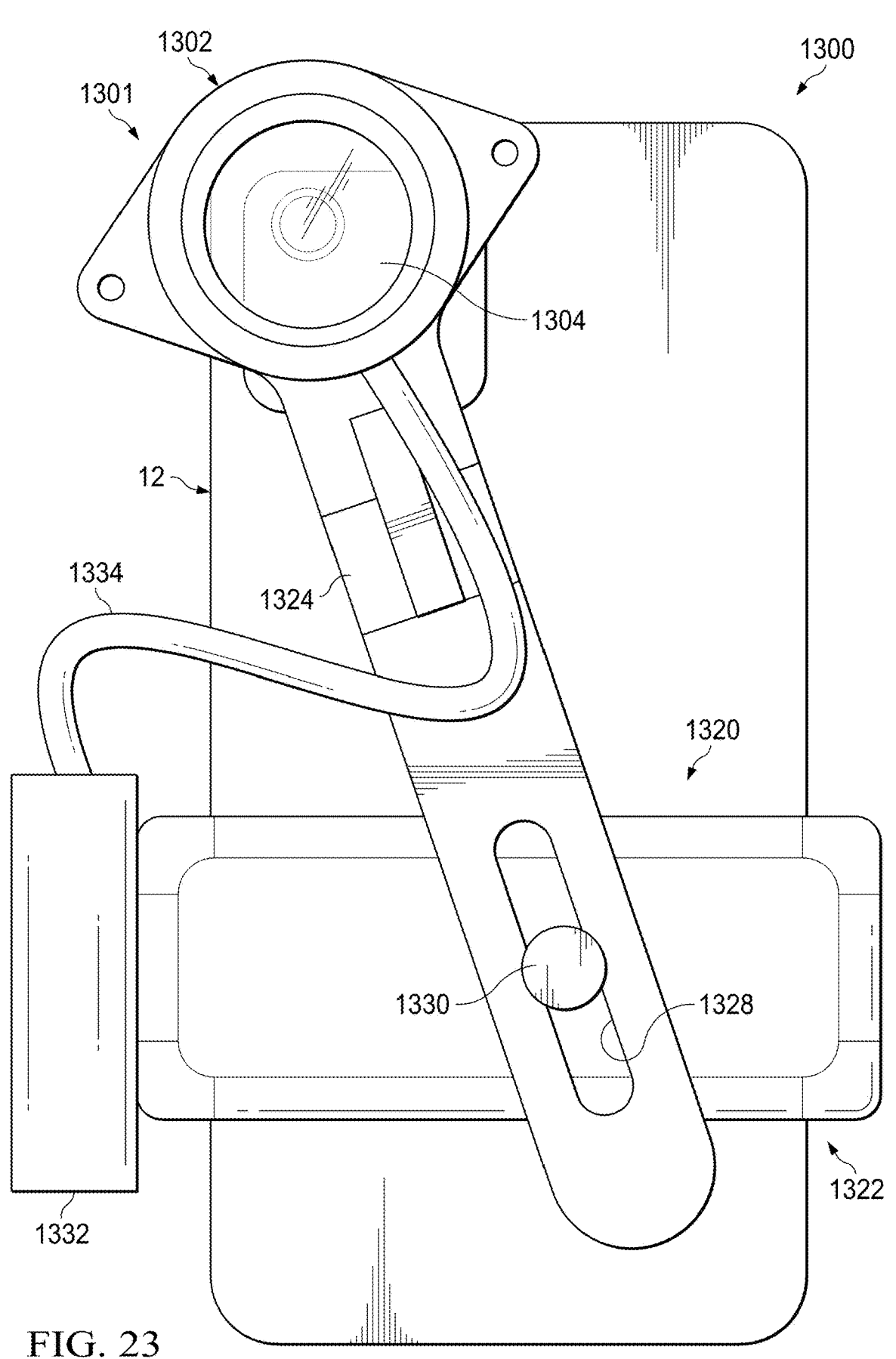
FIG. 23 is rear view of the remote exam system of FIGS. 21 and 22, according to embodiments of the present disclosure.

Referring now to FIGS. 21-23, shown therein is a remote exam system 1300, according to embodiments of the present disclosure. FIG. 21 is a perspective view of the remote exam system 1300, according to embodiments of the present disclosure. FIG. 22 is side view of the remote exam system 1300 of FIG. 21, according to embodiments of the present disclosure. FIG. 23 is rear view of the remote exam system 1300 of FIGS. 21 and 22, according to embodiments of the present disclosure. The remote exam system 1300 may incorporate one or more aspects or features of the remote exam attachments described above with respect to FIGS. 1-4 and 11-18. In some aspects, the example illustrated in FIGS. 21-23 includes features similar to the remote exam systems 900 and 1000 of FIGS. 16 and 17.

The remote exam system 1300 includes a user device 12 and a remote exam attachment 1301. The remote exam attachment 1301 can include a housing 1302. The housing 1302 can include one or more optical elements 1304 (e.g., one or more lenses, mirrors, etc.). In some instances, the housing 1302 may be further configured to interface with a speculum (e.g., the speculums of FIGS. 3, 4, 6A-8B, and/or 16-20). In this regard, a distal portion of the housing 1302 may receive a proximal portion of the speculum via an interference/press fit, snap fit, a threaded engagement, and/or or other engagement type such that the speculum is, at least temporarily, held in a fixed position relative to the housing 1302.

The remote exam system 1300 also includes a mounting structure 1320. The mounting structure 1320 may be utilized to removably couple the housing 1302 (and associated optical element(s)) to the user device 12. In particular, the mounting structure 1320 may be utilized to removably couple the housing 1302 to the user device 12 such that an optical path of the remote exam system 1300 can be aligned with a camera (e.g., front-facing or rear-facing) of the user device 12. The components of the mounting structure may be formed of any suitable material, including plastics and/or metals. As shown, the mounting structure 1320 includes a mounting clamp 1322. The mounting clamp 1322 may be similar to structural body 602 described above with respect to FIG. 13 and/or the mounting clamp 1022 described above with respect to FIGS. 17 and 18.

The mounting structure 1320 may further include an elongated portion 1324 extending from the mounting clamp 1322. The elongated portion 1324 may interface with the housing 1302 and/or be integrally formed with the housing 1302. In some instances, the elongated portion 1324 includes a portion or section sized and shaped to receive and/or couple with a proximal portion of the housing 1302. In some instances, the elongated portion 1324 of the mounting structure is permanently and/or fixedly secured to the housing 1302. As shown, a proximal portion of the elongated portion 1324 includes a slot 1328. The slot 1328 extends linearly along the length of the elongated portion 1324. A screw 1330 (or other selectively locking mechanism) couples the elongated portion 1324 to the mounting clamp 1322. In particular, the screw 1330 extends through the slot 1328 and threadingly engages an opening in the mounting clamp 1322. The interface of the slot 1328 with the screw 1330 allows the elongated portion 1324 to move linearly along the length of the slot 1028 and pivot about the screw 1330 when the screw is loosened. This movement allows a user to adjust the alignment of an optical axis of the remote exam attachment 1301 with a camera of the user device 12. Once the remote exam attachment 1301 is properly aligned relative to the user device 12, the screw 1330 can be tightened to secure the relative position of the remote exam attachment 1301. It will be appreciated that different and/multiple locking mechanisms may be used to hold the position of the remote exam attachment 1301 relative to the user device 12 once the desired alignment is achieved.

The remote exam attachment 1301 also includes a light source 1332 and optical element 1334. In this regard, the light source 1332 and optical element 1334 may be utilized to generate sufficient illumination to inner cavities (e.g., throat, ear, nose, etc.) of the patient to obtain suitable photos and/or videos. The light source 1332 may be any suitable light source, including a fiber optic light source, a laser light source, a light emitting diode (LED), or otherwise. The light source 1332 may include a dedicated and/or integrated power supply (e.g., battery, capacitor, etc.). Alternatively, the light source 1332 may draw power from the user device 12. The optical element 134 may be an optical fiber, a light pipe, an LED, or other suitable component to output light/ energy generated by the light source 1332. In some instances, the optical element 1334 may extend at least partially within the housing 1302. In some instances, the optical element 1334 may be positioned adjacent to, but outside of the housing 1302. Regardless of the positioning of the output of the optical element 1334 (e.g., inside or outside of the housing 1302), the optical element 1334 may be oriented such that the light output illuminates an area/ volume of interest along the optical path of the remote exam attachment 1301. In some instances, the light source 1332 and optical element 1334 are used in lieu of the light source(s) of the user device 12. In other instances, the light source 1332 and optical element 1334 are used in combination with the light source(s) of the user device 12.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A remote medical examination system, comprising:
a remote exam attachment operable to removably couple to a user device,
  wherein the user device, to which the remote exam attachment is operable to removably couple, comprises a front-facing camera;
  wherein the remote exam attachment comprises an optical element; and
  wherein the remote exam attachment is sized and shaped so that the optical element of the remote exam attachment is optically aligned with the front-facing camera of the user device when the remote exam attachment is coupled to the user device;
an external light attachment coupled to the remote exam attachment, the external light attachment comprising:
  a housing; and
  an external light source disposed within the housing; and
a speculum coupled to the remote exam attachment;
  wherein, when the remote exam attachment is coupled to the user device, the front-facing camera of the user device is operable to capture an image of an object using:

the optical element of the remote exam attachment, the external light attachment comprising the housing and the external light source disposed therewithin, and the speculum;

wherein the external light attachment is coupled to the remote exam attachment so that the position of the housing of the external light attachment, which includes the external light source disposed within the housing, is fixed, relative to the remote exam attachment, in each of:

a first direction, a second direction that is perpendicular to the first direction, and a third direction that is perpendicular to each of the first direction and the second direction and thus the second direction is perpendicular to each of the first direction and the third direction;

wherein, when the remote exam attachment is coupled to the user device, the position of the optical element of the remote exam attachment is fixed, relative to the speculum, in each of:

the first direction, the second direction that is perpendicular to each of the first direction and the third direction, and the third direction that is perpendicular to each of the first direction and the second direction;

wherein, when the remote exam attachment is coupled to the user device, the position of the speculum is fixed, relative to the remote exam attachment, in each of:

the first direction, the second direction that is perpendicular to each of the first direction and the third direction, and the third direction that is perpendicular to each of the first direction and the second direction;

wherein, when the remote exam attachment is coupled to the user device, the position of the housing of the external light attachment, which includes the external light source disposed within the housing, is fixed, relative to each of the user device and the remote exam attachment, in each of:

the first direction; and the third direction that is perpendicular to each of the first direction and the second direction, and wherein, when the remote exam attachment is coupled to the user device, the position of the housing of the external light attachment, and thus the external light source disposed within the housing, is adjustable, relative to the user device, in the second direction that is perpendicular to each of the first direction and the third direction.

2. The remote medical examination system of claim 1, wherein the speculum is coupled to the light attachment; and wherein the speculum is coupled to the remote exam attachment via the light attachment.

3. The remote medical examination system of claim 1, wherein the speculum is coupled directly to the remote exam attachment.

4. The remote medical examination system of claim 1, wherein the optical element comprises a lens.

5. The remote medical examination system of claim 1, wherein, when the remote exam attachment is coupled to the user device, the position of the housing of the external light attachment, which includes the external light source disposed within the housing, is fixed, relative to the user device, in each of:

the first direction;

the second direction that is perpendicular to each of the first direction and the third direction; and the third direction that is perpendicular to each of the first direction and the second direction.

6. The remote medical examination system of claim 1, further comprising an application executed by the user device, wherein the application is configured to:

control one or more aspects of the user device or the remote exam attachment to obtain one or more images and/or videos of patient anatomy; and control the one or more aspects of the user device or the remote exam attachment by controlling one or more light settings wherein the one or more light settings include at least one of a light source activation, a light source activation timing, or a light source brightness level.

7. The remote medical examination system of claim 6, wherein the application is further configured to control the one or more aspects of the user device or the remote exam attachment by controlling one or more camera settings.

8. The remote medical examination system of claim 7, wherein the one or more camera settings include at least one of an angular field of view, a depth of focus, a digital zoom parameter, or an image processing parameter.

9. The remote medical examination system of claim 6, wherein the one or more light settings are associated with a light source of the user device.

10. The remote medical examination system of claim 6, wherein the one or more light settings are associated with the external light source.

11. The remote medical examination system of claim 1, wherein the speculum is sized and shaped for use with an ear, and/or a nose, of a patient.

12. The remote medical examination system of claim 1, further comprising a tongue depressor.

13. The remote medical examination system of claim 12, wherein the remote exam attachment comprises the tongue depressor.

14. The remote medical examination system of claim 12, wherein the remote exam attachment comprises an arm and a support coupled to the arm; and wherein the arm and the support are operable to removably couple with the tongue depressor.

15. The remote medical examination system of claim 1, wherein the remote exam attachment is operable to removably couple with a tongue depressor.

16. The remote medical examination system of claim 15, further comprising the tongue depressor with which the remote exam attachment is operably to removably couple.

17. The remote medical examination system of claim 1, wherein the speculum is removably coupled to the remote exam attachment;

wherein the remote medical examination system comprises a plurality of speculums to which the speculum removably coupled to the remote exam attachment belongs; and wherein each speculum of the plurality of speculums is operable to removably couple to the remote exam attachment and each speculum of the plurality of speculums has a different size and/or a different optical property than one or more other speculums of the plurality of speculums.

18. The remote medical examination system of claim 17, further comprising an application executed by the user device, wherein the application is configured to identify the speculum removably coupled to the remote exam attachment by:

detecting the speculum removably coupled to the remote exam attachment; and/or receiving an input identifying the speculum removably coupled to the remote exam attachment.

19. The remote medical examination system of claim 18, wherein the application is configured to:

control, based on the identification of the speculum, one or more aspects of the user device or the remote exam attachment to obtain one or more images and/or videos of patient anatomy; and control the one or more aspects of the user device or the remote exam attachment by controlling one or more light settings wherein the one or more light settings include at least one of a light source activation, a light source activation timing, or a light source brightness level.

* * * * *